United States Patent [19]
Bodmer et al.

[11] Patent Number: 5,965,710
[45] Date of Patent: Oct. 12, 1999

[54] MONOCLONAL ANTIBODIES FOR USE IN DIAGNOSIS AND TREATMENT OF COLORECTAL CANCER

[75] Inventors: Walter F Bodmer, London; Helga Durbin, Watford; David Snary, Orpington; Lorna M D Stewart, Surbiton; Susan Young, London; Paul A Bates, Woodford Green, all of United Kingdom

[73] Assignee: Imperial Cancer Research Technology Limited, London, United Kingdom

[21] Appl. No.: 08/602,725

[22] PCT Filed: Aug. 19, 1994

[86] PCT No.: PCT/GB94/01816

§ 371 Date: Feb. 23, 1996

§ 102(e) Date: Feb. 23, 1996

[87] PCT Pub. No.: WO95/06067

PCT Pub. Date: Mar. 2, 1995

[30] Foreign Application Priority Data

Aug. 21, 1993 [GB] United Kingdom .................. 9317423

[51] Int. Cl.$^6$ .......................... C07K 16/18; C07K 16/30; G01N 33/574
[52] U.S. Cl. .................. 530/387.7; 530/395; 530/387.9; 530/387.3; 435/7.23; 435/172.2; 435/344; 435/330; 424/133.1; 424/155.1
[58] Field of Search .................. 435/172.2, 328, 435/344, 330, 7.23; 530/387.1, 387.3, 387.7, 350, 395, 387.9; 424/130.1, 133.1, 141.1, 155.1

[56] References Cited

FOREIGN PATENT DOCUMENTS 0 323 806  7/1989  European Pat. Off. .

OTHER PUBLICATIONS

Granowska et al., "Radiolabelled monoclonal antibodies in oncology II. Clinical applications in diagnosis", Nuclear Medicine Communications, 12, 83–98 (1991).
Richman et al. "Monoclonal antibodies to human colorectal . . . " Int. J. Cancer 39, pp. 317–328, 1987.
M. Granowska et al. "$^{99m}$Tc radioimmunoscintigraphy of colorectal cancer" B. J. Cancer, 10, pp. 30–33, 1990.
K. Sheahan et al. "Differential Reactivities of carcinoembryonic . . . " Am. J. Clin. Path. 94, pp. 157–164, 1990.
Y. Sakurai et al. "Conformational epitopes specific to carcinoembryonic . . . " J. Surg. Oncol. 42, pp. 39–46, 1989.
H. Durbin et al. "An epitope on carcinoembryonic antigen . . . " Proc. Natl. Acad. Sci. USA 91, pp. 4313–4317, 1994.
M. Granowska et al. "Radioimmunoscintigraphy with technetium–99m . . . " Eur. J. Nucl. Med. 20, pp. 690–698, 1993.
Pignatelli & Bodmer. "Genetics and biochemistry of collagen . . . " Proc. Natl. Aca. Sci USA 85, pp. 5561–5565, 1988.
Richman & Bodmer. "Control of differentiation in human . . . " J. Pathology, 156, pp. 197–211, 1988.
Stürzbecher et al. "p53 interacts with p34$^{cdc2}$ in mammalian . . . " Oncogene 5, pp. 795–801, 1990.
M. Granowska et al. "A new monoclonal antibody for . . . " Nuclear Medicine trends & possibilities in nuclear medicine, Schmidt & Buraggi, eds. Schaltaner, Stuttgart & New York, pp. 531–534, 1989.
M. Pignatelli et a. "Carcinoembryonic antigen functions . . . " Proc. Natl Acad. Sci. USA 87, pp. 1541–1545, 1990.
R.J. Paxton et al. "Sequence analysis of carcinoembryonic . . . " Proc. Natl Acad. Sci. USA 84, pp. 920–924, 1987.
M. Pignatelli et al. "Integrin Cell Adhesion Molecules . . . " Journal of Pathology, vol. 162 (1990), pp. 95–97, 1990.

*Primary Examiner*—Toni R. Scheiner
*Attorney, Agent, or Firm*—Nixon & Vanderhye, P.C.

[57] ABSTRACT

A molecule which (i) binds human membrane-bound carcinoembryonic antigen, (ii) binds a hybrid polypeptide consisting of residues 1 to 314 of human biliary glycoprotein joined (N-C) to residues 490 to C-terminus of human carcino embryonic antigen, but (iii) does not bind to human biliary glycoprotein excluding an intact mouse monoclonal antibody comprising an IgG group IIA heavy chain and a kappa group V light chain wherein the sequence of the $V_H$ chain is QVKLQQSGPELKKP GETVKISCKASGYTFTVFGMNWVKQAPGKGLK WMGWINTKTGEATYVEEFKGRFAFSLETSATTAYLQI NNLKNEDTAKYFCARWDFYDYVEAMDYWGQ TTVTVSS, or wherein the sequence of the $V_H$ chain is as given immediately above but the first amino acid residue of the $V_H$ CDR1 is glutamine and in either case the sequence of the $V_L$ chain is GDIVMTQSQRFMSTSVGDRVSVT CKASQ NVGTNVAWYQQKPGQSPKALIYSASYRYS GPDRFTGSG-SGTDFTLT ISNVQSEDLAEYFCHQYYTYPLFTFGSGTKLEMKR. Preferably the molecule is a monoclonal antibody.

19 Claims, 29 Drawing Sheets

FIG. 1

|              | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| RF-TS3 backbone | Q | V | Q | L | V | Q | S | G | S | E | L | K | K | P | G | A | S | V | K |
| Humanised Heavy | Q | V | Q | L | V | Q | S | G | S | E | L | K | K | P | G | A | S | V | K |
| Murine Heavy    | Q | V | K | L | Q | Q | S | G | P | E | L | K | K | P | G | E | T | V | K |

|              | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|
| RF-TS3 backbone | V | S | C | K | A | S | G | Y | T | F | T | S | Y | A | M | N |
| Humanised Heavy | V | S | C | K | A | S | G | Y | T | F | T | V | F | G | M | N |
| Murine Heavy    | I | S | C | K | A | S | G | Y | T | F | T | V | F | G | M | N |

|              | 36 | 37 | 38 | 39 | 40 | 41 | 42 | 43 | 44 | 45 | 46 | 47 | 48 | 49 |
|---|---|---|---|---|---|---|---|---|---|---|---|---|---|---|
| RF-TS3 backbone | W | V | R | Q | A | P | G | Q | G | L | E | W | M | G |
| Humanised Heavy | W | V | R | Q | A | P | G | Q | G | L | E | W | M | G |
| Murine Heavy    | W | V | K | Q | A | P | G | K | G | L | K | W | M | G |

|              | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| RF-TS3 backbone | W | I | N | T | N | G | N | P | T | Y | A | Q | G | F | T | G |  |
| Humanised Heavy | W | I | N | T | K | T | G | E | A | T | Y | V | E | E | F | K | G |
| Murine Heavy    | W | I | N | T | K | T | G | E | A | T | Y | V | E | E | F | K | G |

|              | 66 | 67 | 68 | 69 | 70 | 71 | 72 | 73 | 74 | 75 | 76 | 77 | 78 | 79 | 80 | 81 | 82 | a | b | c |
|---|---|---|---|---|---|---|---|---|---|---|---|---|---|---|---|---|---|---|---|---|
| RF-TS3 backbone | R | F | V | F | S | L | D | T | S | V | S | T | A | Y | L | Q | I | S | S | L |
| Humanised Heavy | R | F | V | F | S | L | D | T | S | V | S | T | A | Y | L | Q | I | S | S | L |
| Murine Heavy    | R | F | A | F | S | L | E | T | S | A | T | T | A | Y | L | Q | I | N | N | L |

|              | 83 | 84 | 85 | 86 | 87 | 88 | 89 | 90 | 91 | 92 | 93 | 94 |
|---|---|---|---|---|---|---|---|---|---|---|---|---|
| RF-TS3 backbone | K | A | D | D | T | A | V | Y | Y | C | A | R |
| Humanised Heavy | K | A | D | D | T | A | V | Y | Y | C | A | R |
| Murine Heavy    | K | N | E | D | T | A | K | Y | F | C | A | R |

|              | 95 | 96 | 97 | 98 | 99 | 100 | a | b | c | k | 101 |
|---|---|---|---|---|---|---|---|---|---|---|---|
| RF-TS3 backbone | E | D | S | N | G | Y | L | I | - | F | D |
| Humanised Heavy | W | D | F | Y | D | Y | V | E | A | M | D |
| Murine Heavy    | W | D | F | Y | D | Y | V | E | A | N | D |

|              | 102 | 103 | 104 | 105 | 106 | 107 | 108 | 109 | 110 | 111 | 112 | 113 |
|---|---|---|---|---|---|---|---|---|---|---|---|---|
| RF-TS3 backbone | Y | W | D | Q | G | T | L | V | I | V | S | S |
| Humanised Heavy | Y | W | G | Q | G | T | T | V | T | V | S | S |
| Murine Heavy    | Y | W | G | Q | G | T | T | V | T | V | S | S |

FIG. 2

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| REI backbone | D | I | Q | M | T | Q | S | P | S | S | L | S | A | S | V |
| Humanised Kappa | D | I | Q | M | T | Q | S | P | S | S | L | S | A | S | V |
| Murine Kappa | D | I | V | M | T | Q | S | Q | R | F | M | S | T | S | V |

|  | 16 | 17 | 18 | 19 | 20 | 21 | 22 | 23 | 24 | 25 | 26 | 27 | 28 | 29 |
|---|---|---|---|---|---|---|---|---|---|---|---|---|---|---|
| REI backbone | G | D | R | V | T | I | T | C | Q | A | S | Q | D | I |
| Humanised Kappa | G | D | R | V | T | I | T | C | K | A | S | Q | N | V |
| Murine Kappa | G | D | R | V | S | V | T | C | K | A | S | Q | N | V |

|  | 30 | 31 | 32 | 33 | 34 | 35 | 36 | 37 | 38 | 39 | 40 | 41 | 42 | 43 |
|---|---|---|---|---|---|---|---|---|---|---|---|---|---|---|
| REI backbone | I | K | Y | L | A | W | Y | Q | Q | T | P | G | K | A |
| Humanised Kappa | G | T | N | V | A | W | Y | Q | Q | K | P | G | K | A |
| Murine Kappa | G | T | N | V | A | W | Y | Q | Q | K | P | G | Q | S |

|  | 44 | 45 | 46 | 47 | 48 | 49 | 50 | 51 | 52 | 53 | 54 | 55 | 56 |
|---|---|---|---|---|---|---|---|---|---|---|---|---|---|
| REI backbone | P | K | L | L | I | Y | E | A | S | N | L | Q | A |
| Humanised Kappa | P | K | L | L | I | Y | S | A | S | Y | R | Y | S |
| Murine Kappa | P | K | A | L | I | Y | S | A | S | Y | R | Y | S |

|  | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|
| REI backbone | G | V | P | S | R | F | S | G | S | G | S | G | T | D | Y |
| Humanised Kappa | G | V | P | S | R | F | S | G | S | G | S | G | T | D | F |
| Murine Kappa | G | V | P | D | R | F | T | G | S | G | S | G | T | D | F |

|  | 72 | 73 | 74 | 75 | 76 | 77 | 78 | 79 | 80 | 81 | 82 | 83 | 84 | 85 | 86 |
|---|---|---|---|---|---|---|---|---|---|---|---|---|---|---|---|
| REI backbone | T | F | T | I | S | S | L | Q | P | E | D | I | A | T | Y |
| Humanised Kappa | T | F | T | I | S | S | L | Q | P | E | D | I | A | T | Y |
| Murine Kappa | T | L | T | I | S | N | V | Q | S | E | D | L | A | E | Y |

|  | 87 | 88 | 89 | 90 | 91 | 92 | 93 | 94 | 95 | 95a | 96 | 97 |
|---|---|---|---|---|---|---|---|---|---|---|---|---|
| REI backbone | Y | C | Q | Q | Y | Q | S | L | P | - | Y | T |
| Humanised Kappa | Y | C | H | Q | Y | Y | T | Y | P | L | F | T |
| Murine Kappa | F | C | H | Q | Y | Y | T | Y | P | L | F | T |

|  | 98 | 99 | 100 | 101 | 102 | 103 | 104 | 105 | 106 | 107 | 108 |
|---|---|---|---|---|---|---|---|---|---|---|---|
| REI backbone | F | G | Q | G | T | K | I | E | I | T | R |
| Humanised Kappa | F | G | Q | G | T | K | V | E | I | K | R |
| Murine Kappa | F | G | S | G | T | K | L | E | M | K | R |

FIG. 3

```
                     -34
CEA leader           MESPSAPPHRWCIPWQRLLLTASLLTFWNPPTTA
NCA leader           .GP.L...C.LHV..KEV...............

1
CEA N-terminus       KLTIESTPFNVAEGKEVLLLVHNLPQHLFGYSWYKGERVDGNRQIIGVIGTQQATPGPA
                     .................A......NRI.............SL.V..............

108
                     YSGREIIYPNASLLIQNIIQNDTGFYTLHVIKSDLVNEEATGQFRVYP
                     ........T.........VT....Q.............H....

CEA repeat 1   109   ELPKPSISSNNSKPVEDKDAVAFTCEPETQDATYLWWVNNQSLPVSPRLQLSNGNRTLTL
CEA repeat 2   287   .P...F.T...N...E....L....I.NT.........D................
CEA repeat 3   465   ................A.NT.........G.....................
NCA repeat           ................N.NT.........G..........M........

FNVTRNDTASYKCETQNPVSARRSDSVILNVLYGPDAPTISPLNTSYRSGENLNLSCHAA     286
                     LS....VGP.E.GI..EL.VDH.P.........D....SY.Y..P.V..S........    464
                     ......ARA.V.GI..S...N...P.T.D......T.I...PDS..L..A......S.    642
                     LS.K...AG..E.I...A..N...P.T......G.......SKAN..P..........

SNPPAQYSWFVNGTFQQSTQELFIPNITVNNSGSYTCQAHNSDTGLNRTTVTTITVYA     286
                     .......LID.NI..H......S...EK..L....N..AS.HS...K....S.       464
                     ...SP....RI..IP..H..V...AK..P..N.T.A.FVS.LA..R.NSI.KS...S.   642
                     .............IT....................M.....A........M...SG

CEA C-terminus 643   SGTSPGLSAGATVGIMIGVLVGVALI   668
NCA C-terminus       --SA.V...V.....T....AR.....
```

FIG. 4-1

```
ATG GGG CAC CTC TCA GCC CCA CTT CAC AGA GTG CGT GTA CCC TGG CAG          48
Met Gly His Leu Ser Ala Pro Leu His Arg Val Arg Val Pro Trp Gln
 1                    5                  10                  15

GGG CTT CTG CTC ACA GCC TCA CTT CTA ACC TTC TGG AAC CCG ACC              96
Gly Leu Leu Leu Thr Ala Ser Leu Leu Thr Phe Trp Asn Pro Thr
                 20                  25                  30

ACT GCC CAG CTC ACT ACT GAA TCC ATG CCA TTC AAT GTT GCA GAG GGG         144
Thr Ala Gln Leu Thr Thr Glu Ser Met Pro Phe Asn Val Ala Glu Gly
         1          35                  40                  45

AAG GAG GTT CTT CTC CTT GTC CAC AAT CTG CCC CAG CAA CTT TTT GGC         192
Lys Glu Val Leu Leu Leu Val His Asn Leu Pro Gln Gln Leu Phe Gly
        16          50                  55                  60

TAC AGC TGG TAC AAA GGG GAA AGA GTG GAT GGC AAC CGT CAA ATT GTA         240
Tyr Ser Trp Tyr Lys Gly Glu Arg Val Asp Gly Asn Arg Gln Ile Val
65                  70                  75                  80

GGA TAT GCA ATA GGA ACT CAA CAA GCT ACC CAA GGG CCC GCA AAC AGC         288
Gly Tyr Ala Ile Gly Thr Gln Gln Ala Thr Pro Gly Pro Ala Asn Ser
                 85                  90                  95
```

FIG. 4-2

```
GGT CGA GAG ACA ATA TAC CCC AAT GCA TCC CTG CTG ATC CAG AAC GTC    336
Gly Arg Glu Thr Ile Tyr Pro Asn Ala Ser Leu Leu Ile Gln Asn Val
         66                      105                     110

ACC CAG AAT GAC ACA GGA TTC TAC ACC CTA CAA GTC ATA AAG TCA GAT    384
Thr Gln Asn Asp Thr Gly Phe Tyr Thr Leu Gln Val Ile Lys Ser Asp
        115                      120                 125

CTT GTG AAT GAA GCA ACT GGA CAG TTC CAT GTA TAC CCG GAG CTG        432
Leu Val Asn Glu Ala Thr Gly Gln Phe His Val Tyr Pro Glu Leu
        130                      135                 140

CCC AAG CCC ATC TCC AGC AAC AAC TCC AAC CCT GTG GAG GAC AAG        480
Pro Lys Pro Ile Ser Ser Asn Asn Ser Asn Pro Val Glu Asp Lys
145                     116        155                     160

GAT GCT GTG GCC TTC ACC TGT GAA CCT GAG ACT CCG GTC AGT CCC AGG    528
Asp Ala Val Ala Phe Thr Cys Glu Pro Glu Thr Pro Val Ser Pro Arg
                 165                     170                 175

CTG TGG TGG ATA AAC AAT CAG AGC CTC AGC CTC AGT CCC AGG CTG CAG    576
Leu Trp Trp Ile Asn Asn Gln Ser Leu Ser Leu Pro Val Ser Pro Arg Leu Gln
        180                      185                 190

CTG TCC AAT GGC AAC AGG ACC CTC ACT CTA CTC AGT GTC ACA AGG AAT    624
Leu Ser Asn Gly Asn Arg Thr Leu Thr Leu Leu Ser Val Thr Arg Asn
        195                     166                      205
```

FIG. 4-3

```
GAC ACA GGA CCC TAT GAG TGT GAA ATA CAG AAC CCA GTG AGT GCG AAC    672
Asp Thr Gly Pro Tyr Glu Cys Glu Ile Gln Asn Pro Val Ser Ala Asn
210                 215                 220

CGC AGT GAC CCA GTC ACC TTG AAT GTC ACC TAT TAT GGC CCG GAC ACC CCC    720
Arg Ser Asp Pro Val Thr Leu Asn Val Thr Tyr Tyr Gly Pro Asp Thr Pro
225                 230                 235                 240

ACC ATT TCC CCT TCA GAC ACC TAT TAC CGT CCA GGG GCA AAC CTC AGC    768
Thr Ile Ser Pro Ser Asp Thr Tyr Tyr Arg Pro Gly Ala Asn Leu Ser
245                 250        216              255

CTC TCC TGC TAT GCA GCC TCT AAC CCA CCT GCA CCT CAG TAC TCC TGG CTT    816
Leu Ser Cys Tyr Ala Ala Ser Asn Pro Pro Ala Gln Tyr Ser Trp Leu
260                 265                 270

ATC AAT GGA ACA TTC CAG CAA AGC ACA GAG CTC TTT ATC CCT AAC    864
Ile Asn Gly Thr Phe Gln Gln Ser Thr Glu Leu Phe Ile Pro Asn
275                 280                 285

ATC ACT GTG AAT AAT AGT GGA TCC TAT ACC TGC CAC GCC AAT AAC TCA    912
Ile Thr Val Asn Asn Ser Gly Ser Tyr Thr Cys His Ala Asn Asn Ser
290                 295                 300        266

GTC ACT GGC TGC AAC AGG ACC ACA GTC AAG ACG ATC ATA GTC ACT GAG    960
Val Thr Gly Cys Asn Arg Thr Thr Val Lys Thr Ile Ile Val Thr Glu
305                 310                 315                 320
```

FIG. 4-4

```
CTA AGT CCA GTA GTA GCA AAG CCC CAA ATC AAA GCC AGC AAG ACC ACA      1008
Leu Ser Pro Val Val Ala Lys Pro Gln Ile Lys Ala Ser Lys Thr Thr
            325                 330                 335

GTC ACA GGA GAT AAG GAC TCT GTG AAC CTG ACC TGC TCC ACA AAT GAC      1056
Val Thr Gly Asp Lys Asp Ser Val Asn Leu Thr Cys Ser Thr Asn Asp
            340                 345                 316

ACT GGA ATC TCC ATC CGT TGG TTC TTC AAA AAC CAG AGT CTC CCG TCC      1104
Thr Gly Ile Ser Ile Arg Trp Phe Phe Lys Asn Gln Ser Leu Pro Ser
            355                 360                 365

TCG GAG AGG ATG AAG CTG TCC CAG GGC AAC ACC ACC CTC AGC ATA AAC      1152
Ser Glu Arg Met Lys Leu Ser Gln Gly Asn Thr Thr Leu Ser Ile Asn
            370                 375                 380

CCT GTC AAG AGG GAG GAT GCT GGG ACG TAT TGG TGT GAG GTC TTC AAC      1200
Pro Val Lys Arg Glu Asp Ala Gly Thr Tyr Trp Cys Glu Val Phe Asn
            385                 390                 395                 366

CCA ATC AGT AAG AAC AAC CAA AGC GAC CCC ATC ATG CTG AAC GTA TAT      1248
Pro Ile Ser Lys Asn Asn Gln Ser Asp Pro Ile Met Leu Asn Val Tyr
            405                 410                 415

AAT GCT CTA CCA CAA GAA AAT GGC CTC TCA CCT GGG GCC ATT GCT GGC      1296
Asn Ala Leu Pro Gln Glu Asn Gly Leu Ser Pro Gly Ala Ile Ala Gly
            420                 425                 430
```

FIG. 4-5

```
ATT GTG ATT GGA GTA GTG GCC CTG GTT GCT CTG ATA GCA GTA GCC CTG    1344
Ile Val Ile Gly Val Val Ala Leu Val Ala Leu Ile Ala Val Ala Leu
             435                 440                 445

GCA TGT TTT CTG CAT TTC GGG AAG ACC GGC AGC TCA GGA CCA CTC CAA    1392
Ala Cys Phe Leu His Phe Gly Lys Thr Gly Ser Ser Gly Pro Leu Gln
416                          455                 460         430

TGACCCACCT AACAAGATGA ATGAAGTTAC TTATCTACCC TGAACTTTGA AGCCCAGCAA  1452

CCCACACAAC CAACTTCACT T                                            1473
```

FIG. 8
| Schematic representation | Residues | PR1A3 reactivity |
|---|---|---|
BGP
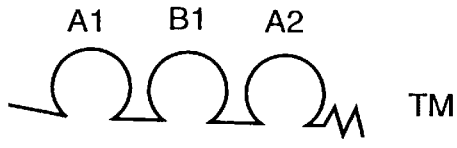
430 —
CEA
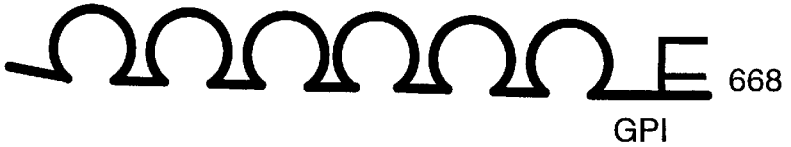
668 +
1) BGP-CEA chimera
BGP:1-314
CEA:490-668   +
2) secreted chimera
BGP:1-314
CEA:490-643   —
3) chimera + transmembrane domain
BGP:1-314
CEA:490-643
BGP:391-430   —

FIG. 11-1

```
ATG GGA CCC CCC TCA GCC CCT CCC TGC AGA TTG CAT GTC CCC TGG AAG    48
Met Gly Pro Pro Ser Ala Pro Pro Cys Arg Leu His Val Pro Trp Lys
 1                   5                  10                  15

GAG GTC CTG CTC ACA GCC TCA CTT CTA ACC TTC TGG AAC CCA CCC ACC    96
Glu Val Leu Leu Thr Ala Ser Leu Leu Thr Phe Trp Asn Pro Pro Thr
                    20                  25                  30

ACT GCC AAG CTC ACT ATT GAA TCC ACG CCA TTC AAT GTC GCA GAG GGG   144
Thr Ala Lys Leu Thr Ile Glu Ser Thr Pro Phe Asn Val Ala Glu Gly
                    35                  40                  45

AAG GAG GTT CTT CTA CTC GCC CAC AAC CTG CCC CAG AAT CGT ATT GGT   192
Lys Glu Val Leu Leu Leu Ala His Asn Leu Pro Gln Asn Arg Ile Gly
                    50                  55                  60

TAC AGC TGG TAC AAA GCG GAA AGA GTG GAT GGC AAC AGT CTA ATT GTA   240
Tyr Ser Trp Tyr Lys Ala Glu Arg Val Asp Gly Asn Ser Leu Ile Val
                    65                  70                  75                  80

GGA TAT GTA ATA GGA ACT CAA CAA GCT ACC CCA GGG CCC GCA TAC AGT   288
Gly Tyr Val Ile Gly Thr Gln Gln Ala Thr Pro Gly Pro Ala Tyr Ser
                    85                  90                  95
```

FIG. 11-2

```
GGT CGA GAG ACA ATA TAC CCC AAT GCA TCC CTG CTG ATC CAG AAC GTC    336
Gly Arg Glu Thr Ile Tyr Pro Asn Ala Ser Leu Leu Ile Gln Asn Val
100                 105                 110

ACC CAG ATT GAC ACA GGA TTC TAT ACC CTA CAA GTC ATA AAG TCA GAT    384
Thr Gln Ile Asp Thr Gly Phe Tyr Thr Leu Gln Val Ile Lys Ser Asp
        115                 120                 125

CTT GTG AAT GAA GCA ACC GGA CAG TTC CAT GTA TAC CCG GAG CTG        432
Leu Val Asn Glu Ala Thr Gly Gln Phe His Val Tyr Pro Glu Leu
130                 135                 140

CCC AAG CCC TCC ATC TCC AGC AAC AAC TCC AAC CCC GTG GAG GAC AAG    480
Pro Lys Pro Ser Ile Ser Ser Asn Asn Ser Asn Pro Val Glu Asp Lys
145                 150                 155                 160

GAT GCT GTG GCC TTC ACC TGT GAA CCT GAG GTT CAG AAC ACA ACC TAC    528
Asp Ala Val Ala Phe Thr Cys Glu Pro Glu Val Gln Asn Thr Thr Tyr
        165                 170                 175

GTC TGG TGG GTA AAT GGT CAG AGC CTC CCG GTC AGT CCC AGG CTG CAG    576
Val Trp Trp Val Asn Gly Gln Ser Leu Pro Val Ser Pro Arg Leu Gln
180                 185                 190

CTG TCC AAT GGC AAC ATG ACC CTC ACT CTA CTC AGC GTC AAA AGG AAC    624
Leu Ser Asn Gly Asn Met Thr Leu Thr Leu Leu Ser Val Lys Arg Asn
        195                 200                 205
```

FIG. 11-3

```
GAT GCA GGA TCC TAT GAA TGT GAA ATA CAG AAC CCA GCG AGT GCC AAC      672
Asp Ala Gly Ser Tyr Glu Cys Glu Ile Gln Asn Pro Ala Ser Ala Asn
210                 215                 220

CGC AGT GAC CCA GTC ACC CTG AAT GTC CTC TAT GGC CCA GAT GGC CCC      720
Arg Ser Asp Pro Val Thr Leu Asn Val Leu Tyr Gly Pro Asp Gly Pro
    225                 230                 235                 240

ACC ATT TCC CCC TCA AAG GCC AAT TAC CGT CCA GGG GAA AAT CTG AAC      768
Thr Ile Ser Pro Ser Lys Ala Asn Tyr Arg Pro Gly Glu Asn Leu Asn
        245                 250                 255

CTC TCC CAC TCG CAC GCA GCC TCT AAC CCA CCT GCA CAG TAC TCT TGG TTT  816
Leu Ser His Ser His Ala Ala Ser Asn Pro Pro Ala Gln Tyr Ser Trp Phe
            260                 265                 270

ATC AAT GGG ACG TTC CAG CAA TCC ACA CAA GAG CTC TTT ATC CCC AAC      864
Ile Asn Gly Thr Phe Gln Gln Ser Thr Gln Glu Leu Phe Ile Pro Asn
    275                 280                 285

ATC ACT GTG AAT AAT AGC GGA TCC TAT ATG TGC CAA GCC CAT AAC TCA      912
Ile Thr Val Asn Asn Ser Gly Ser Tyr Met Cys Gln Ala His Asn Ser
290                 295                 300

GCC ACT GGC CTC AAT AGG ACC ACA GTC ACG ATC ACA GTC TCT GGA          960
Ala Thr Gly Leu Asn Arg Thr Thr Val Thr Ile Thr Val Ser Gly
305                 310                 315                 320
```

FIG. 11-4

```
AGT GCT CCT GTC CTC TCA GCT GTG GCC ACC GTC GGC ATC ACG ATT GGA    1008
Ser Ala Pro Val Leu Ser Ala Val Ala Thr Val Gly Ile Thr Ile Gly
              325                     330                335

GTG CTG GCC AGG GTC GCT CTG ATA TAGCAGCCCT GGTGTATTTT CGATATTTCA   1062
Val Leu Ala Arg Val Ala Leu Ile
              340

GGAAGACTGG CAGATTGGAC CAGACCCTGA ATTCTTCTAG C                      1103
```

FIG. 12-1

```
TCG GCC CCT CCC CAC AGA TGG TGC ATC CCC TGG CAG AGG CTC CTG CTC    48
Ser Ala Pro His Arg Trp Cys Ile Pro Trp Gln Arg Leu Leu Leu
 1               5                  10                  15

ACA GCC TCA CTT CTA ACC TTC TGG AAC CCG ACC ACT GCC AAG CTC        96
Thr Ala Ser Leu Leu Thr Phe Trp Asn Pro Thr Thr Ala Lys Leu
            20                  25                  30   1

ACT ATT GAA TCC ACG CCG TTC AAT GTC GCA GAG GGG AAG GAG GTG CTT   144
Thr Ile Glu Ser Thr Pro Phe Asn Val Ala Glu Gly Lys Glu Val Leu
        35                  40                  45

CTA CTT GTC CAC AAT CTG CAG CAT CTT TTT GGC TAC AGC TGG TAC       192
Leu Leu Val His Asn Leu Gln His Leu Phe Gly Tyr Ser Trp Tyr
    50                  55                  60

AAA GGT GAA AGA GTG GAT GGC AAC CGT CAA ATT ATA GGA TAT GTA ATA   240
Lys Gly Glu Arg Val Asp Gly Asn Arg Gln Ile Ile Gly Tyr Val Ile
65                  70                  75                  80

GGA ACT CAA CAA GCT ACC CCA GGG CCC GCA TAC AGT GGT CGA GAG ATA   288
Gly Thr Gln Gln Ala Thr Pro Gly Pro Ala Tyr Ser Gly Arg Glu Ile
        85                  90                  95

ATA TAC CCC AAT GCA TCC CTG CTG ATC ATC CAG AAC GAT           336
Ile Tyr Pro Asn Ala Ser Leu Leu Ile Ile Gln Asn Asp
```

FIG. 12-2

```
                100                   105                   110
ACA GGA TTC TAC ACC CTA CAC GTC ATA AAG TCA GAT CTT GTG AAT GAA    384
Thr Gly Phe Tyr Thr Leu His Val Ile Lys Ser Asp Leu Val Asn Glu
115                     120                   125

GAA GCA ACT GGC CAG TTC CGG GTA TAC CCG GAG CTG CCC AAG CCC TCC    432
Glu Ala Thr Gly Gln Phe Arg Val Tyr Pro Glu Leu Pro Lys Pro Ser
130                     135                108 109 140

ATC TCC AGC AAC AAC TCC AAA CCC GTG GAG GAC AAG GAT GCT GTG GCC    480
Ile Ser Ser Asn Asn Ser Lys Pro Val Glu Asp Lys Asp Ala Val Ala
145                     150                   155                   160

TTC ACC TGT GAA CCT GAG ACT CAG GAC GCA ACC TAC CTG TGG TGG GTA    528
Phe Thr Cys Glu Pro Glu Thr Gln Asp Ala Thr Tyr Leu Trp Trp Val
                165                   170                   175

AAC AAT CAG AGC CTC CCG GTC AGT CCC CGG GTC AGT AGG CTG CAG CTG TCC AAT GGC    576
Asn Asn Gln Ser Leu Pro Val Ser Pro Arg Val Ser Arg Leu Gln Leu Ser Asn Gly
180                     185                   190

AAC AGG ACC ACT CTA ACT TTC AAT GTC ACA AGA AAT GAC ACA GCA AGC    624
Asn Arg Thr Thr Leu Thr Phe Asn Val Thr Arg Asn Asp Thr Ala Ser
195                     200                   205

TAC AAA TGT GAA ACC CAG AAC CCA GTG AGT GCC AGG CGC AGT GAT TCA    672
Tyr Lys Cys Glu Thr Gln Asn Pro Val Ser Ala Arg Arg Ser Asp Ser
```

FIG. 12-3

```
              210           215             220
GTC ATC CTG AAT GTC CTC TAT GGC CCG GAT GCC CCC ACC ATT TCC CCT    720
Val Ile Leu Asn Val Leu Tyr Gly Pro Asp Ala Pro Thr Ile Ser Pro
225                 230             235             240

CTA AAC ACA TCT TAC AGA TCA GGG GAA AAT CTG AAC CTC TCC TGC CAC    768
Leu Asn Thr Ser Tyr Arg Ser Gly Glu Asn Leu Asn Leu Ser Cys His
        245             250             255

GCA GCC TCT AAC CCA CCT GCA CAG TAC TCT TGG TTT GTC AAT GGG ACT    816
Ala Ala Ser Asn Pro Pro Ala Gln Tyr Ser Trp Phe Val Asn Gly Thr
260             265             270

TTC CAG CAA ACC CAA GAG CTC TTT ATC CCC AAC ATC ACT GTG AAT        864
Phe Gln Gln Thr Gln Glu Leu Phe Ile Pro Asn Ile Thr Val Asn
    275             280             285

AAT AGT GGA TCC TAT ACG TGC CAA GCC CAT AAC AGC GAC ACT GGC CTC    912
Asn Ser Gly Ser Tyr Thr Cys Gln Ala His Asn Ser Asp Thr Gly Leu
290             295             300

AAT AGG ACC ACA GTC ACG ACA ATC ACA GTC TAT GCA GAG CCA CCC AAA    960
Asn Arg Thr Thr Val Thr Thr Ile Thr Val Tyr Ala Glu Pro Pro Lys
305             310             315  286  287       320

CCC TTC ATC ACC AGC AAC AAC TCC AAC CCC GTG GAG GAT GAG GAT GCT   1008
Pro Phe Ile Thr Ser Asn Asn Ser Asn Pro Val Glu Asp Glu Asp Ala
```

FIG. 12-4

```
GTA GCC TTA ACC TGT GAA CCT GAG ATT CAG AAC ACA ACC TAC CTG TGG    1056
Val Ala Leu Thr Cys Glu Pro Glu Ile Gln Asn Thr Thr Tyr Leu Trp
340                 325             345         330        350        335

TGG GTA AAT CAG AGC CTC CCG AGT CCC AGG CTG CAG CTG TCC            1104
Trp Val Asn Gln Ser Leu Pro Ser Pro Arg Leu Gln Leu Ser
    355                 360                 365

AAT GAC AAC AGG ACC CTC CTA CTC ACT AGT GTC ACA AGG AAT GAT GTA    1152
Asn Asp Asn Arg Thr Leu Leu Leu Thr Ser Val Thr Arg Asn Asp Val
        370                 375                 380

GGA CCC TAT GAG TGT GGA ATC GGG GAA TTA AGT GTT GAC CAC AGC        1200
Gly Pro Tyr Glu Cys Gly Ile Gly Glu Leu Ser Val Asp His Ser
385                 390                 395             400

GAC CCA GTC ATC CTG AAT GTC CTC TAT GGC CCA GAC GAC CCC ACC ATT    1248
Asp Pro Val Ile Leu Asn Val Leu Tyr Gly Pro Asp Asp Pro Thr Ile
        405                 410                 415

TCC CCC TCA TAC ACC TAT TAC CGT CCA GGG GTG AAC CTC AGC CTC TCC    1296
Ser Pro Ser Tyr Thr Tyr Tyr Arg Pro Gly Val Asn Leu Ser Leu Ser
    420                 425                 430

TGC CAT GCA GCC TCT AAC CCA CCT GCA CAG TAT TCT TGG CTG ATT GAT    1344
Cys His Ala Ala Ser Asn Pro Pro Ala Gln Tyr Ser Trp Leu Ile Asp
```

FIG. 12-5

```
                435               440               445
GGG AAC ATC CAG CAA CAC ACA CAA GAG CTC TTT ATC TCC AAC ATC ACT    1392
Gly Asn Ile Gln Gln His Thr Gln Glu Leu Phe Ile Ser Asn Ile Thr
450                 455                 460

GAG AAG AAC AGC GGA CTC TAT ACC TGC CAG GCC AAT AAC TCA GCC AGT    1440
Glu Lys Asn Ser Gly Leu Tyr Thr Cys Gln Ala Asn Asn Ser Ala Ser
465                 470                 475                 480

GGC CAC AGC AGG ACT ACA GTC AAG ACA ATC ACA GTC TCT GCG GAG CTG    1488
Gly His Ser Arg Thr Thr Val Lys Thr Ile Thr Val Ser Ala Glu Leu
            485                 490                 464  465

CCC AAG CCC TCC ATC TCC AGC AAC AAC TCC AAA CCC GTG GAG GAC AAG    1536
Pro Lys Pro Ser Ile Ser Ser Asn Asn Ser Lys Pro Val Glu Asp Lys
        500                 505                 510

GAT GCT GTG GCC TTC ACC TGT GAA CCT GAG GCT GCA GTC ACC TAC        1584
Asp Ala Val Ala Phe Thr Cys Glu Pro Glu Ala Ala Val Thr Thr Tyr
515                 520                 525

CTG TGG GTA AAT GGT CAG CAG AGC CTC CCA GTC AGT CCC AGG CTG CAG    1632
Leu Trp Val Asn Gly Gln Gln Ser Leu Pro Val Ser Pro Arg Leu Gln
530                 535                 540

CTG TCC AAT GGC AAC AGG ACC CTC ACT CTA TTC AAT GTC ACA AGA AAT    1680
Leu Ser Asn Gly Asn Arg Thr Leu Thr Leu Phe Asn Val Thr Arg Asn
```

FIG. 12-6

```
    545              550              555              560
GAC GCA AGA GCC TAT GTA TGT GGA ATC CAG AAC TCA GTG AGT GCA AAC   1728
Asp Ala Arg Ala Tyr Val Cys Gly Ile Gln Asn Ser Val Ser Ala Asn
                565              570              575

CGC AGT GAC CCA GTC ACC CTG GAT GTC CTC TAT GGG CCG GAC ACC CCC   1776
Arg Ser Asp Pro Val Thr Leu Asp Val Leu Tyr Gly Pro Asp Thr Pro
        580              585              590

ATC ATT TCC CCC CCA GAC TCG TCT TAC CTT TCG GGA GCG AAC CTC AAC   1824
Ile Ile Ser Pro Pro Asp Ser Ser Tyr Leu Ser Gly Ala Asn Leu Asn
    595              600              605

CTC TCC TGC CAC TCG GCC TCT AAC CCA TCC CCG CAG TAT TCT TGG CGT   1872
Leu Ser Cys His Ser Ala Ser Asn Pro Ser Pro Gln Tyr Ser Trp Arg
610              615              620

ATC AAT GGG ATA CCG CAG CAA CAC ACA CAA GTT CTC TTT ATC GCC AAA   1920
Ile Asn Gly Ile Pro Gln Gln His Thr Gln Val Leu Phe Ile Ala Lys
625              630              635              640

ATC ACG CCA AAT AAT AAC GGG ACC TAT GCC TAT GTC TCT AAC TTG       1968
Ile Thr Pro Asn Asn Asn Gly Thr Tyr Ala Tyr Val Ser Asn Leu
        645              650              655

GCT ACT GGC CGC AAT AAT TCC ATA GTC AAG AGC ATC ACA GTC TCT GCA   2016
Ala Thr Gly Arg Asn Asn Ser Ile Val Lys Ser Ile Thr Val Ser Ala
                                                              642
```

FIG. 12-7

```
TCT GGA ACT TCT CCT GGT CTC TCA GCT GGG GCC ACT GTC GGC ATC ATG    2064
Ser Gly Thr Ser Pro Gly Leu Ser Ala Gly Ala Thr Val Gly Ile Met
643  675              660         680    665         670    685

ATT GGA GTG CTG GTT GGG GTT GCT CTG ATA TAG                        2097
Ile Gly Val Leu Val Gly Val Ala Leu Ile
     690              695              668
```

FIG. 13-1

```
ATG GGC ATC AAG ATG GAG TCA CAT TCC CTG GTC TTT GTA TAC ATG TTG        48
Met Gly Ile Lys Met Glu Ser His Ser Leu Val Phe Val Tyr Met Leu
 1               5                  10                  15

CTG TGG TTG TCT GGT GTT GAT GGA GAC ATT GTG ATG ACC CAG TCT CAA        96
Leu Trp Leu Ser Gly Val Asp Gly Asp Ile Val Met Thr Gln Ser Gln
            20                  25                  30

AGA TTC ATG TCC ACA TCA GTA GGA GAC AGG GTC AGC GTC ACC TGC AAG       144
Arg Phe Met Ser Thr Ser Val Gly Asp Arg Val Ser Val Thr Cys Lys
35                  40                  45

GCC AGT CAG AAT GTG GGT ACT AAT GTT GCC TGG TAT CAA CAG AAA CCA       192
Ala Ser Gln Asn Val Gly Thr Asn Val Ala Trp Tyr Gln Gln Lys Pro
50                  55                  60

GGA CAA TCC CCT AAA GCA CTG ATT TAC TCG GCA TCC TAC CGG TAC AGT       240
Gly Gln Ser Pro Lys Ala Leu Ile Tyr Ser Ala Ser Tyr Arg Tyr Ser
65                  70                  75                  80

GGA GTC CCT GAT CGC TTC ACA GGC AGT GGA TCT GGG ACA GAT TTC ACT       288
Gly Val Pro Asp Arg Phe Thr Gly Ser Gly Ser Gly Thr Asp Phe Thr
            85                  90                  95
```

FIG. 13-2

```
CTC ACC ATC AGC AAT GTA CAG TCT GAA GAC TTG GCG GAG TAT TTC TGT    336
Leu Thr Ile Ser Asn Val Gln Ser Glu Asp Leu Ala Glu Tyr Phe Cys
        100                 105                 110

CAC CAA TAT TAC ACC TAT CCT CTA TTC ACG TTC GGC TCG GGG ACA AAG    384
His Gln Tyr Tyr Thr Tyr Pro Leu Phe Thr Phe Gly Ser Gly Thr Lys
        115                 120                 125

TTG GAA ATG AAA                                                    396
Leu Glu Met Lys
        130
```

FIG. 14-1

```
ATG GGA TGG AGC TGT ATC ATG CTC TTC TTG GCA GCA ACA GCT ACA GGT      48
Met Gly Trp Ser Cys Ile Met Leu Phe Leu Ala Ala Thr Ala Thr Gly
 1               5                  10                  15

GTC CAC TCC CAG GTG AAG CTG CAG CAG TCA GGA CCT GAG TTG AAG AAG      96
Val His Ser Gln Val Lys Leu Gln Gln Ser Gly Pro Glu Leu Lys Lys
            20                  25                  30

CCT GGA GAG ACA GTC AAG ATC TCC TGC AAG GCT TCT GGA TAT ACC TTC     144
Pro Gly Glu Thr Val Lys Ile Ser Cys Lys Ala Ser Gly Tyr Thr Phe
        35                  40                  45

ACA GTG TTT GGA ATG AAC TGG GTG AAG CAG GCT CCT GGA AAG GGT TTA     192
Thr Val Phe Gly Met Asn Trp Val Lys Gln Ala Pro Gly Lys Gly Leu
    50                  55                  60

AAG TGG ATG GGC TGG ATA AAC ACC AAA ACT GGA GAG GCA ACA TAT GTT     240
Lys Trp Met Gly Trp Ile Asn Thr Lys Thr Gly Glu Ala Thr Tyr Val
65                  70                  75                  80

GAA GAG TTT AAG GGA CGG TTT GCC TTC TCT TTG GAG ACC TCT GCC ACC     288
Glu Glu Phe Lys Gly Arg Phe Ala Phe Ser Leu Glu Thr Ser Ala Thr
                85                  90                  95
```

FIG. 14-2

```
ACT GCC TAT TTG CAG ATC AAC AAC CTC AAA AAT GAG GAC ACG GCT AAA          336
Thr Ala Tyr Leu Gln Ile Asn Asn Leu Lys Asn Glu Asp Thr Ala Lys
        100                 105                 110

TAT TTC TGT GCA AGA TGG GAC TTC TAT GAT TAC GTG GAG GCT ATG GAC          384
Tyr Phe Cys Ala Arg Trp Asp Phe Tyr Asp Tyr Val Glu Ala Met Asp
        115                 120                 125

TAC TGG GGC CAA GGG ACC ACG GTC ACC GTC TCC                              417
Tyr Trp Gly Gln Gly Thr Thr Val Thr Val Ser
        130                 135
```

MONOCLONAL ANTIBODIES FOR USE IN DIAGNOSIS AND TREATMENT OF COLORECTAL CANCER

This application is a 371 of PCT/GB94/01816, filed Aug. 19, 1994.

The present invention relates to antibodies useful in diagnosing and treating colorectal cancer.

Antibodies are known that react with carcino-embryonic antigen (CEA), but they react with both membrane-associated CEA and soluble CEA and so are not especially useful in diagnosing colorectal cancer.

Monoclonal antibody PR1A3 was raised by fusion of NS1 (P3/NS1/I-Ag-4-1) myeloma cells with spleen cells from mice immunised with normal colorectal epithelium (Richman & Bodmer 1987). PR1A3 reacts strongly to both well and poorly differentiated colorectal carcinomas and has advantages over other colorectal epithelium-reactive antibodies since its antigen appears fixed to the tumour and does not appear in the lymphatics or normal lymph nodes draining a tumour (Granowska et al 1989). PR1A3 reacted with 59/60 colorectal tumours (Richman & Bodmer 1987), whereas CEA reactive B72.3 reacted with only 75% (Salvatore et al 1989). Although there is some evidence for weak binding to normal cells of the stomach, ileum, oesophagus, trachea and breast, in vivo studies have shown that the basement membrane prevents access by the antibody to these tissues (Granowska et al 1990).

Sheahan et al (1990) *Am. J. Clin. Path.* 94, 157–164 discusses two monoclonal antibodies (D14 and B7.1) which appear to be specific for carcino embryonic antigen.

Sakurai et al (1989) *J. Surg. Oncol.* 42, 39–46 discusses various monoclonal antibodies which appear to be specific for carcino embryonic antigen.

PR1A3 has been distributed publicly, as immunoglobulin, although the hybridoma has not been made available. The precise epitope to which PR1A3 binds has not previously been known.

The present invention seeks to provide further molecules, including monoclonal antibodies with the same or better specificity for colorectal cancer as PR1A3. Such antibodies may be prepared by raising MAbs to the newly discovered PR1A3 epitope which we have now found is part of the carcino-embryonic antigen (CEA), a tumour marker expressed in colorectal carcinomas.

A first aspect of the present invention provides a molecule which (i) binds membrane-bound human carcinoembryonic antigen (CEA), (ii) binds a hybrid polypeptide consisting of residues 1 to 314 of human biliary glycoprotein (BGP) joined (N-C) to residues 490 to C-terminus of intact human CEA, but (iii) does not bind to human BGP, but excluding an intact mouse monoclonal antibody comprising an $IgG_1$ group IIA heavy chain and a kappa group V light chain wherein the sequence of the $V_H$ chain is QVKLQQSGPELKKPGETVKISCKASGYT-
FTVFGMNWVKQAPGKGLKWMGWINTKTGEATY
VEEFKGRFAFSLETSATTAYL-
QINNLKNEDTAKYFCARWDFYDYEAMYWGQGTTVTVS
S        (SEQ ID No 1)

,or wherein the sequence of the $V_H$ chain is as given immediately above but the first amino acid residue of the $V_H$ CDR1 is glutamine and in either case the sequence of the $V_L$ chain is GDIVMTQSQRFMSTSVGDRVSVTCK-
ASQNVGTNVAWYQQKPGQSPKALIYSASYRYSGVP
DRFTGSGSGTDFTLTISNVQSEDLAEY-
FCHQYYTYPLFTFGSGTKLEMKR    (SEQ ID No 2)

The sequence of the $V_H$ chain can also be written as:

Gln Val Lys Leu Gln Gln Ser Gly Pro Glu Leu Lys Lys Pro Gly Glu

Thr Val Lys Ile Ser Cys Lys Ala Ser Gly Tyr Thr Phe Thr Val Phe

Gly Met Asn Trp Val Lys Gln Ala Pro Gly Lys Gly Leu Lys Trp Met

Gly Trp Ile Asn Thr Lys Thr Gly Glu Ala Thr Tyr Val Glu Glu Phe

Lys Gly Arg Phe Ala Phe Ser Leu Glu Thr Ser Ala Thr Thr Ala Tyr

Leu Gln Ile Asn Asn Leu Lys Asn Glu Asp Thr Ala Lys Tyr Phe Cys

Ala Arg Trp Asp Phe Tyr Asp Tyr Val Glu Ala Met Asp Tyr Trp Gly

Gln Gly Thr Thr Val Thr Val Ser Ser

The sequence of the $V_L$ chain can also be written as:

Gly Asp Ile Val Met Thr Gln Ser Gln Arg Phe Met Ser Thr Ser Val

Gly Asp Arg Val Ser Val Thr Cys Lys Ala Ser Gln Asn Val Gly Thr

Asn Val Ala Trp Tyr Gln Gln Lys Pro Gly Gln Ser Pro Lys Ala Leu

Ile Tyr Ser Ala Ser Tyr Arg Tyr Ser Gly Val Pro Asp Arg Phe Thr

Gly Ser Gly Ser Gly Thr Asp Phe Thr Leu Thr Ile Ser Asn Val Gln

Ser Glu Asp Leu Ala Glu Tyr Phe Cys His Gln Tyr Tyr Thr Tyr Pro

Leu Phe Thr Phe Gly Ser Gly Thr Lys Leu Glu Met Lys Arg

The first amino acid residue of the $V_H$ CDR1 is a position 31 in the $V_H$ sequence given.

It is preferred if the molecule is an antibody.

The hybrid polypeptide consisting of the N-A1-B1-(N-terminal half of A2) domains of BGP joined (N-C) to the (C-terminal half of A3)-B3-GPI domains of human CEA is described in detail in Example 1 and shown diagrammatically as chimaera 1 in FIG. 8. It consists of residues 1 to 314 of BGP fused to residues 490—C-terminus of CEA in a N-C fashion. The C-terminus of intact CEA is residue 668.

By "membrane-bound" we mean CEA as found in a colon carcinoma cell, for example the HT-29 cell line, a moderately well-differentiated grade II human colon adenocarcinoma cell line available from the American Type Culture Collection, 12301 Parklawn Drive, Rockville, Md. 20852, USA under catalogue number ATCC HTB 38.

By "binding" we mean that, when assessed by indirect immunofluorescence of acetone-fixed CEA-positive cell monolayers grown in cover slips, a positive signal is seen following incubation with a fluorescence conjugate anti-mouse (or human) IgG antibody. Example 7 describes a method of acetone fixation of cells and determination of binding.

That an antibody heavy chain is $IgG_1$ can be determined by reaction with antisera specific for the isotype sera in immunodiffusion gels (Ouchterlony technique) or by enzyme-linked immunosorbent assays (ELISA). Monoclonal antibodies which react against, and are diagnostic for, mouse IgG heavy chain are commercially available, for example the rat monoclonal antibody clone name LO-MG1-2 available from Serotec, 22 Bankside, Station Approach, Kidlington, Oxford OX5 1JE, UK, and has an avidity of $9 \times 10^8$ $M^{-1}$.

That an antibody light chain is kappa can be determined by reaction with specific antisera in immunodiffusion gels and by ELISA. Monoclonal antibodies which react against, and are diagnostic for, mouse kappa light chain are commercially available, for example the rat monoclonal antibody clone name MRC OX-20 available from Serotec.

IgG group IIA and kappa group V refer to sub-types of the V-regions and are defined by the sequence of the V-region frameworks as described by Kabat et al (1991) *Sequence of Proteins of Immunological Interest,* fifth edition, US Department of Health and Human Services, NIH Publication No 91-3242 incorporated herein by reference.

It is preferred if the molecule does not bind substantially to other naturally occurring human proteins that are present in the human body and whose location is in the bowel. Such proteins include collagen and serum albumin. It is preferred if the molecule does not bind to N-A1-Fc, N-A1-B1-Fc or N-A1-B1-A2-Fc where in A1, B1 and A2 are domains of CEA and Fc is the Fc portion of immunoglobulin.

It is further preferred if the molecule does not bind a B3 hybrid wherein the GPI anchor is removed or wherein the GPI anchor is replaced with a BGP transmembrane segment.

When the molecule is an antibody it is preferred if it comprises a human framework region and at least the complementarity determining regions of the $V_H$ chain and $V_L$ chain as defined in claim 1 wherein for the $V_H$ chain CDR1 is VFGMN (SEQ ID No 3), CDR2 is WINTKTGEATYVEEFKG (SEQ ID No 4) and CDR3 is WDFYDYVEAMDY (SEQ ID No 5) and for the $V_L$ chain CDR1 is KASQNVGTNVA (SEQ ID No 6), CDR2 is SASYRYS (SEQ ID No 7) and CDR3 is HQYYTYPLFT (SEQ ID No 8).

PR1A3 is a mouse monoclonal antibody comprising an $IgG_1$ group IIA heavy chain and a kappa group V light chain wherein the sequence of the $V_H$ chain is as stated above in the exclusion from the first aspect of the invention or wherein the first amino acid residue of the $V_H$ CDR1 is glutamine and the sequence of the $V_L$ chain is as stated above in the exclusion from the first aspect of the invention.

CEA is a member of the immunoglobulin super-gene family (reviewed in Thompson & Zimmermann 1988; Thompson et al 1991). CEA has a domain structure of N-A1-B1-A2-B2-A3-B3-GPI where GPI is a glycophosphatidylinositol membrane anchor. A significant degree of sequence homology exists between the domains of CEA and with other members of the family such as NCA.

Biliary glycoprotein (BGP) is also a member of the immunoglobulin gene super-family and has a domain structure of N-A1-B1-A2-TM, where TM is a transmembrane domain, but the domains A1, B1 and A2 of BGP are not identical to those named A1, B1 and A2 in CEA.

By "antibody", we include monoclonal and polyclonal antibodies and we include antibody fragments which bind specifically but reversibly to (i) human CEA, (ii) a hybrid polypeptide consisting of residues 1 to 314 of human BGP joined (N-C) to residues 490 to C-terminus of human CEA but (iii) do not bind to human BGP excluding an intact mouse monoclonal antibody comprising an IgG1 group IIA heavy chain and a kappa group V light chain wherein the sequence of the $V_H$ chain is (as defined in FIG. 1) or wherein the first amino acid residue of the $V_H$ CDR1 is glutamine and the sequence of the $V_L$ chain (is as defined in FIG. 2).

It is preferred if the antibody or antibody fragment is derived from a monoclonal antibody.

Monoclonal antibodies may be prepared generally by the techniques of Zola, H. (1988) (*"Monoclonal Antibodies—A manual of techniques"* CRC Press) which is incorporated herein by reference. Antibody fragments such as Fab, (Fab)$_2$, Fv, scFv or dAb fragments may be prepared therefrom in known ways. The antibodies may be humanized in known ways for example, by inserting the CDR regions of mouse antibodies into the framework of human antibodies. Antibody-like molecules may be prepared using the recombinant DNA techniques of WO 84/03712. The region specific for the protein may be expressed as part of a bacteriophage, using the technique of McCafferty et al (1990) *Nature* 348, 552–554.

Antibody-like molecules of the invention may be selected from phage display libraries using the methods described in Griffiths et al (1993) *EMBO J.* 12, 725–734 where CEA or hybrid proteins expressed in cells are immobilized and used to select phages. Also, appropriate cells grown in monolayers and either fixed with formaldehyde or glutaraldehyde or unfixed can be used to bind phages. Irrelevant phages are washed away and bound phages recovered by disrupting their binding to the CEA or hybrid protein and reamplifying in bacteria. This selection and amplification process is done several times to enrich the phage population for those molecules which are the antibody-like molecules of the invention.

We also include peptides selected from random peptide libraries in a similar way to those from phage display libraries in the antibody-like molecules of the invention.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Nat. Acad. Sci. USA* 81, 6851–6855) or "CDR grafting" can be used to humanise rodent antibodies. Additionally or alternatively, recombinant monoclonal antibodies may be "primatised", ie antibodies formed in which the variable region of the heavy and light chains, or parts thereof, and the constant regions are derived from two different primate species, preferably the variable regions of the antibody from the macaque monkey, and the constant regions from human. The advantages of such antibodies include high homology to human immunoglobulin, presence of human effector functions, reduced immunogenicity and longer serum half-life (Newman et al (1992) *Biotechnology* 10, 1455).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293–299.

By "ScFv molecules" we mean molecules wherein the $V_H$ and $V_L$ partner domains are linked via a flexible oligopeptide.

In certain circumstances there are advantages of using antibody fragments, rather than whole antibodies. The smaller size of the fragments allows for rapid clearance, and may lead to improved tumour to non-tumour ratios. Fab, Fv, ScFv and dAb antibody fragments can all be expressed in and secreted from *E. coli,* thus allowing the facile production of large amounts of the said fragments.

Whole antibodies, and F(ab')$_2$ fragments are "bivalent". By "bivalent" we mean that the said antibodies and F(ab')$_2$) fragments have two antigen combining sites. In contrast, Fab, Fv, ScFv and dAb fragments are monovalent, having only one antigen combining site.

The art of "antibody engineering" is advancing rapidly, as is described in Tan, L. K. and Morrison, S. L. (1988) *Adv. Drug Deliv. Rev.* 2: 129–142, Williams, G. (1988) *Tibtech* 6: 36–42 and Neuberger, M. S. et al (1988) 8*th International Biotechnology Symposium Part* 2, 792–799 (all of which are incorporated herein by reference), and is well suited to preparing antibody-like molecules derived from the antibodies of the invention.

The antibodies may be used for a variety of purposes relating to the study or isolation and purification of the antigen to which they specifically bind and the imaging and treatment of cells exhibiting the antigen. In other embodiments, the antibody of the invention is coupled to a scintigraphic radiolabel, a cytotoxic compound or radioisotope, an enzyme for converting a non-toxic prodrug into a cytotoxic drug, a compound for activating the immune system in order to target the resulting conjugate to a colon tumour, or a cell-stimulating compound. Such conjugates have a "binding portion", which consists of the antibody of the invention, and a "functional portion", which consists of the radiolabel, toxin or enzyme etc.

The antibody may alternatively be used alone in order simply to block the activity of the CEA antigen, particularly by physically interfering with its binding of another compound.

The binding portion and the functional portion of the conjugate (if also a peptide or polypeptide) may be linked together by any of the conventional ways of cross-linking polypeptides, such as those generally described in O'Sullivan et al (1979) *Anal. Biochem.* 100, 100–108. For example, one portion may be enriched with thiol groups and the other portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, if the binding portion contains carbohydrates, such as would be the case for an antibody or some antibody fragments, the functional portion may be linked via the carbohydrate portion using the linking technology in EP 0 088 695.

The functional portion of the conjugate may be an enzyme for converting a non-toxic prodrug into a toxic drug, for example the conjugates of Bagshawe and his colleagues (Bagshawe (1987) *Br. J. Cancer* 56, 531; Bagshawe et al (1988) *Br. J. Cancer* 58, 700; WO 88/07378) or cyanide-releasing systems (WO 91/11201).

It may not be necessary for the whole enzyme to be present in the conjugate but, of course, the catalytic portion must be present. So-called "abzymes" may be used, where a monoclonal antibody is raised to a compound involved in the reaction one wishes to catalyse, usually the reactive intermediate state. The resulting antibody can then function as an enzyme for the reaction.

The conjugate may be purified by size exclusion or affinity chromatography, and tested for dual biological activities. The antigen immunoreactivity may be measured using an enzyme-linked immunosorbent assay (ELISA) with immobilised antigen and in a live cell radio-immunoassay. An enzyme assay may be used for β-glucosidase using a substrate which changes in absorbance when the glucose residues are hydrolysed, such as oNPG (o-nitrophenyl-β-D-glucopyranoside), liberating 2-nitrophenol which is measured spectrophotometrically at 405 nm.

Stability of the conjugate may be tested in vitro initially by incubating at 37° C. in serum, followed by size exclusion FPLC analysis. Stability in vivo can be tested in the same way in mice by analysing the serum at various times after injection of the conjugate. In addition, it is possible to radiolabel the antibody with $^{125}$I, and the enzyme with $^{131}$I before conjugation, and to determine the biodistribution of the conjugate, free antibody and free enzyme in mice.

Alternatively, the conjugate may be produced as a fusion compound by recombinant DNA techniques whereby a length of DNA comprises respective regions encoding the two portions of the conjugate either adjacent one another or separated by a region encoding a linker peptide which does not destroy the desired properties of the conjugate.

Conceivably, the two functional portions of the compound may overlap wholly or partly. The DNA is then expressed in a suitable host in known ways.

The conjugates may be administered in any suitable way, usually parenterally, for example intravenously or intraperitoneally, in standard sterile, non-pyrogenic formulations of diluents and carriers, for example isotonic saline (when administered intravenously). Once the conjugate has bound to the target cells and been cleared from the bloodstream (if necessary), which typically takes a day or so, the pro-drug is administered, usually as a single infused dose, or the tumour is imaged.

If needed, because the conjugate may be immunogenic, cyclosporin or some other immunosuppressant can be administered to provide a longer period for treatment but usually this will not be necessary.

The timing between administrations of conjugate and pro-drug may be optimised in a non-inventive way since tumour/normal tissue ratios of conjugate (at least following intravenous delivery) are highest after about 4–6 days, whereas at this time the absolute amount of conjugate bound to the tumour, in terms of percent of injected dose per gram, is lower than at earlier times.

Therefore, the optimum interval between administration of the conjugate and the pro-drug will be a compromise between peak tumour concentration of enzyme and the best distribution ratio between tumour and normal tissues. The dosage of the conjugate will be chosen by the physician according to the usual criteria. At least in the case of methods employing a targeted enzyme such as β-glucosidase and intravenous amygdalin as the toxic pro-drug, 1 to 50 daily doses of 0.1 to 10.0 grams per square meter of body surface area, preferably 1.0–5.0 g/m$^2$ are likely to be appropriate. For oral therapy, three doses per day of 0.05 to 10.0 g, preferably 1.0–5.0 g, for one to fifty days may be appropriate. The dosage of any conjugate will similarly be chosen according to normal criteria, particularly with reference to the type, stage and location of the tumour and the weight of the patient. The duration of treatment will depend in part upon the rapidity and extent of any immune reaction to the conjugate.

The functional portion of the conjugate, when the conjugate is used for diagnosis, usually comprises and may consist of a radioactive atom for scintigraphic studies, for example technetium 99 m ($^{99m}$Tc) or iodine-123 ($^{123}$I), or a spin label for nuclear magnetic resonance (nmr) imaging (also known as magnetic resonance imaging, mri), such as iodine-123 again, iodine-131, indium-111, fluorine-19, carbon-13, nitrogen-15, oxygen-17, gadolinium, manganese or iron.

When used in a compound for selective destruction of the tumour, the functional portion may comprise a highly radioactive atom, such as iodine-131, rhenium-186, rhenium-188, yttrium-90 or lead-212, which emits enough energy to destroy neighbouring cells, or a cytotoxic chemical compound such as methotrexate, adriamicin, vinca alkaloids (vincristine, vinblastine, etoposide), daunorubicin or other intercalating agents.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can be attached via a cysteine residue in the peptide. Yttrium-90 can be attached via a lysine residue. The IODOGEN method (Fraker et al (1978) *Biochem. Biophys. Res. Commun.* 80: 49–57 can be used to incorporate iodine-123. *"Monoclonal Antibodies in Immunoscintigraphy"* (Chatal, CRC Press 1989) describes other methods in detail.

Thus, a second aspect of the invention provides a molecule, preferably an antibody, as defined in the first aspect of the invention for use in medicine.

A third aspect of the invention provides a use of a molecule, preferably antibody, as defined by the first aspect of the invention in the manufacture of a medicament for use in the diagnosis or treatment of colorectal carcinoma.

A fourth aspect of the invention provides a process for making a monospecific antibody, the process comprising screening a pool of antibodies to select those monospecific antibodies which bind (i) human membrane-based CEA, (ii) bind a hybrid polypeptide consisting of residues 1 to 314 of human BGP joined (N-C) to residues 490 to C-terminus of human CEA, but (iii) do not bind to human BGP.

It is preferred if the monospecific antibody is a monoclonal antibody and the pool of antibodies is a pool of monoclonal antibodies. It is further preferred if the antibodies within the pool comprise antibodies produced by recombinant DNA methods.

In the preferred embodiment the screening steps are for antibodies that:
(1) Bind to human tumour cells such as colorectal carcinoma cells (Richman & Bodmer (1987) *Int. J. Cancer* 39, 317–328) and the human gastric carcinoma cell line MKN 45 (Kojama et al (1990) *Jpn. J. Cancer* 81, 967–970). Binding is detected in indirect immunofluorescent assays where the cells are fixed to microscope slides or cover slips, for example with acetone, and antibody binding detected by a second fluorescently-labelled anti-species antibody, for example a FITC labelled anti-mouse IgG if the first antibody is a mouse IgG. Alternatively antibody binding to cells in suspension could be measured; and antibody binding could be detected by radioactively-labelled second antibody, for example by $^{125}$I-labelled anti-mouse IgG.
(2) Bind to cells transfected with and expressing the human CEA. For example, these could be the simian virus 40-transformed monkey fibroblast line COS-7 transfected by electroporation with a CEA cDNA (Beauchemin et al (1987) *Mol. Cell. Biol.* 7, 3221–3230) in the vector pCDM8 (Invitrogen); Chinese hamster ovary cells (CHO) transfected by electroporation with a CEA cDNA in the dexamethasone inducible vector pMAMneo (Clontech): a cosmid clone for CEA (Wilicocks, T. C. & Craig, I. W. (1990) *Genomics* 8, 492–500) co-transfected into the mouse colorectal carcinoma cell line CMT93 by lipofection with the plasmid pSVneo2; CHO cells transfected with a yeast artificial chromosome or YAC containing the CEA gene cluster, eg ICRFy9000C02400 from the q13.1–q13.3 region of the long arm of chromosome 19 and modified to include a neomycin resistance (neo$^R$) gene by homologous recombination with the plasmid vector pRAN4 (Ragoussis et al (1992) *Nucleic Acids Res.* 290, 3135–3138) with the right hand vector arm of pYAC4, transfection could be by yeast spheroplast cell fusion (Burgers, P. & Percival, K. (1987) *Anal. Biochem* 163, 391–397).
(3) Bind to cells transfected with and expressing the hybrid gene BGP-CEAB3-GP1, for example COS-7 cells transfected by electroporation with the plasmid pCDM8 carrying the hybrid gene. Electroporation is described in Example 6.
(4) Do not bind to cells expressing BGP but not expressing CEA, for example COS-7 cells transfected with the plasmid pCDM8 carrying the cDNA for BGP.
(5) Do not bind to cells expressing NCA but not expressing CEA, for example COS-7 cells transfected with the plasmid pCDM8 carrying the cDNA for NCA (Hefta et al (1990) *Cancer Res.* 50, 2397–2403).
(6) Do not bind to cells expressing the hybrid BGP-CEAB3 but without the GPI anchor, these cells could be transfected COS-7 cells transfected with the plasmid pCDM8 carrying the hybrid gene for BGP-CEAB3 where a stop codon is introduced into the CEAB3 sequence at the beginning of the position of the hydrophobic tail which is normally processed off and replaced by a GPI anchor. PCR can be used to introduce such a stop codon.
(7) Do not bind to a cell expressing BGP-CEAB3-BGP TM, for example COS-7 transected with pCDM8 carrying the hybrid gene where the transmembrane domain of BGP was added to the B3 domain of CEA in place of the processed hydrophobic segment of CEA.

A useful control antibody that does not bind CEA is one that, for example, recognises the T-cell marker CD4. Suitable anti-CD4 antibodies are available from the ATCC, for example OKT4 (anti-human helper T cell subset; ATCC CRL 8002).

Selecting the antibodies of the invention can be done using the above steps in any permutation.

It is preferred if primary screening is done on a CEA-expressing cell line which can be a human tumour cell line or a transfectoma expressing CEA from a cDNA or cosmid.

It is preferred if secondary screening is done on cell lines transfected with the above mentioned genes and hybrid genes.

NCA is non-specific cross reacting antigen and comprises N, A1 and B1 domains and a GPI anchor (see Thomson & Zimmerman (1988) *Tumour Biol.* 9, 63–83 and Thomson et al (1991) *J. Clin. Lab. Analysis* 5, 344–366 for reviews).

Suitable parent cell lines for expression include COS cells and CHO cells which do not express CEA.

BRIEF DESCRIPTION OF THE DRAWINGS

The invention will now be described in detail with reference to the following Examples and Figures wherein:

FIG. 1 shows the deduced amino acid sequence for the $V_H$ chain of murine monoclonal antibody (murine heavy; SEQ ID No 1), its comparison with the $V_H$ sequence of the human antibody RF-TS3'CL used to provide the framework sequences for humanisation (RF-TS3 backbone; SEQ ID No 27), and the humanised sequence created (humanised heavy; SEQ ID No 28). The sequence of RF-TS3'CL is disclosed in Pascual et al (1990) *J. Clin. Invest.* 86, 1320–1328 incorporated herein by reference.

FIG. 2 shows the deduced amino acid sequence for the $V_L$ chain of murine monoclonal antibody (murine kappa; SEQ ID No 2), its comparison with the $V_L$ sequence of the human antibody REI used to provide the framework sequences for humanisation (REI backbone; SEQ ID No 29), and the humanised sequence created (humanised kappa; SEQ ID No 30).

FIG. 3 shows the amino acid sequence comparison between CEA and NCA-50. Corresponding domains are grouped together. In each case, dots indicate identity to the amino acids of the CEA domains shown in the top line of each group. Dashes indicate amino acid deletions in comparison with CEA. Potential N-glycosylation positions are underlined.

FIG. 4 shows the cDNA sequence (SEQ ID No 31) and deduced amino acid sequence (SEQ ID No 32) of BGP.

FIG. 8 shows the BGP-CEA chimaeric constructs.

FIG. 11 shows the cDNA sequence (SEQ ID No 33) and deduced amino acid sequence (SEQ ID No 34) of NCA.

FIG. 12 shows the cDNA sequence (SEQ ID No 35) and deduced amino acid sequence (SEQ ID No 36) of CEA.

FIG. 13 shows the cDNA sequence (SEQ ID No 37) and deduced amino acid sequence (SEQ ID No 38) of the PR1A3 kappa light chain.

FIG. 14 shows the cDNA sequence (SEQ ID No 39) and deduced amino acid sequence (SEQ ID No 40) of the PR1A3 heavy chain.

EXAMPLE 1

Figure 5:
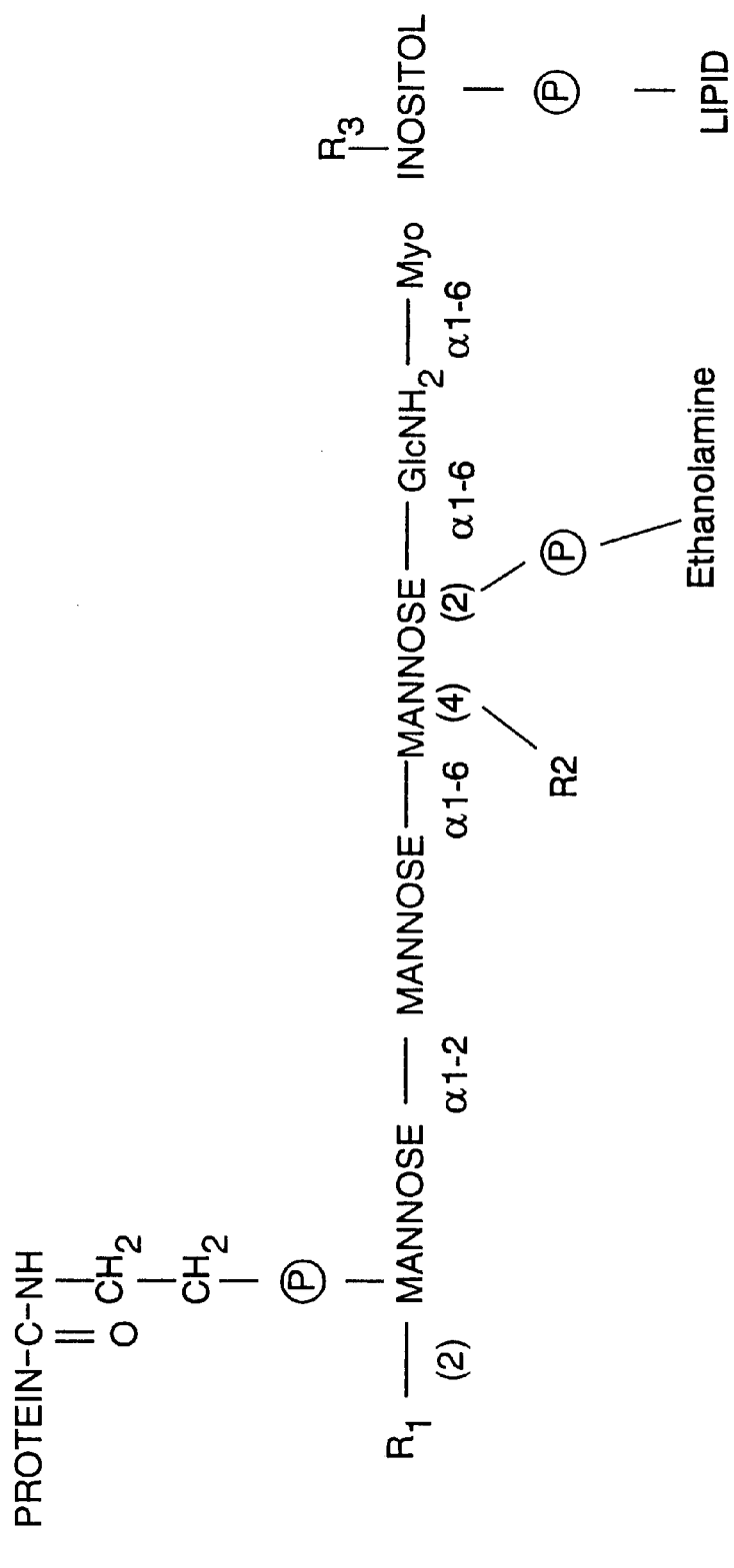
FIG. 5 shows the structures of GPI.

Identification of the Epitope Recognised by PR1A3

YAC (yeast artificial chromosome) and cosmid studies have mapped the gene encoding the PR1A3 antigen to the chromosomal region in which the CEA gene is located and, like CEA, the PR1A3 epitope was shown to be up-regulated by γ-interferon. Transfection of a cDNA for CEA into a variety of cells gave the appearance of the PR1A3 epitope on these cells, thus indicating that the monoclonal antibody PR1A3 recognises an epitope on CEA.

Domains of CEA were expressed in COS cells as fusions to the Fc portion of immunoglobulin as N-A1-Fc, N-A1-B1-Fc and N-A1-B1-A2-Fc. None of these constructs produced protein which reacted with PR1A3, therefore the epitope is not located in the N-A1-B1-A2 region.

Hybrid constructs of BGP and CEA were made such that the (C-terminal half of A3)-B3-GPI domains of CEA were fused to the N-A1-B1-(N-terminal half of A2) domains of BGP. Amino acid sequences for CEA and BGP are shown in FIGS. 3 and 4. The hybrid construct number 1 contained BGP up to cysteine 314 and from glutamic acid 490 to the C-terminus of CEA (see FIG. 8). The hybrid construct was expressed in COS cells from the expression plasmid pCDM8. When analysed in immunofluorescence assays the transfected COS cells gave a positive signal with both the mouse PR1A3 antibody and a human/mouse chimaeric antibody (see below). This confirms that the PR1A3 epitope is in the region of the B3-GPI region. The plasmid pCDM8 is described in Seed & Aruffo (1987) *Proc. Natl. Acad. Sci. USA* 84, 3365–3369.

A stop codon was inserted into the hybrid construct number 1 such that no GPI anchor was added to the protein. The CEA portion should no longer be membrane bound but soluble and secreted. The stop codon was inserted at a position equivalent to residue 644 of CEA and a protein of (N-A1-B1-(N-terminal half of A2)) BGP—((C-terminal half of A3)-B3) CEA was formed (construct number 2; FIG. 8). Transfection of this construct into COS cells using the vector pCDM8 gave cells which were positive in immunofluorescent studies with an antibody, 3B10, which cross-reacts with BGP, but negative for PR1A3. This confirms expression of the hybrid protein but that the PR1A3 epitope is absent when the hybrid is not membrane bound.

Chimaeric constructs 3a and 3b were made and the structures are as indicated in FIG. 8.

PCR methods used in making expression constructs

For cloning BGP the following primers were used:

| 5' + HindIII site: | CTCAAGCTTATGGGGCACCTC (SEQ ID No 9) |
|---|---|
| 3' + XbaI site: | GGTCTAGACTATGAAGTTGGTTG (SEQ ID No 10) |

For cloning CEA the following primers were used:

| 5' + HindIII site: | CTCAAGCTTATGGAGTCTCCC (SEQ ID No 11) |
|---|---|
| 3' + XbaI site: | GGTCTAGACTATATCAGAGCAAC (SEQ ID No 12) |

For chimaera 1 BGP and CEA fragments were amplified by PCR from parent molecules. Products were cut with ClaI and ligated. 5' and 3' ends of the annealed product were cut with HindIII and XbaI for ligation into the HindIII-XbaI site of pCDM8 vector for transient expression in COS-7 cells.

The following primers were used:

| 5' + HindIII site: | CTCAAGCTTATGGGGCACCTC (SEQ ID No 9) |
|---|---|
| 3' B1 loop + ClaI site: | GGATCGATGCAGGTCAGGTT (SEQ ID No 13) |
| 5' IIIA loop + ClaI site: | CTCATCGATGAACCTGAGGCT (SEQ ID No 14) |
| 3' + XbaI site: | GGTCTAGACTATATCAGAGCAAC (SEQ ID No 15) |

Chimaera 2 was amplified from chimaera 1 and cut with HindIII and XbaI for ligation into pCDM8.

The following primers were used:

| 5' + HindIII site: | CTCAAGCTTATGGGGCACCTC (SEQ ID No 9) |
|---|---|
| 3' + STOP + XbaI site: | GGTCTAGACTAAGATGCAGAGAC (SEQ ID No 16) |

For making chimaeras 3a and 3b 5' portion of the molecule was amplified from chimaera 1 template using BGP 5' primer and antisense overlapping primer complementary to the required join. The BGP transmembrane domain was amplified from BGP using sense overlapping primer and BGP 3' primer.

To assemble the annealed molecule, the two complementary fragments were subjected to 18 PCR cycles to allow formation of "primer-dimer" before addition of BGP 5' and 3' outside primers for 12 further PCR cycles.

The following primers were used for construct 3a:

| 5' + HindIII site: | CTCAAGCTTATGGGGCACCTC (SEQ ID No 9) |
|---|---|
| Overlapping primers: | TCTGCATCTGGACTCTCACCTGGGGCC (sense) (SEQ ID No 17) GGCCCCAGGTGAGAGTCCAGATGCAGA (antisense) (SEQ ID No 18) |
| 3' + XbaI site: | GGTCTAGACTATGAAGTTGGTTG (SEQ ID No 10) |

The following primers were used for construct 3b:

| 5' + HindIII site: | CTCAAGCTTATGGGGCACCTC (SEQ ID No 9) |
|---|---|
| Overlapping primers: | ACAGTCTCTGCACAAGAAAATGGC (sense) (SEQ ID No 19) GCCATTTTCTTGTGCAGAGACTGT (antisense) (SEQ ID No 20) |
| 3' + XbaI site: | GGTCTAGACTATGAAGTTGGTTG (SEQ ID No 10) |

Anchor structures are reviewed in Ferguson (1992) and a generic structure for a mammalian GPI is shown in FIG. 5. Studies with CEA released from MKN45 cells by incubation with a phospholipase, which cleaves the lipid tail from GPI anchors to give a soluble product, produces CEA which contains the PR1A3 epitope. When examined by SDS PAGE and western blotting a weak signal is given if this antigen is boiled in 2% SDS sample buffer with reducing agent dithiothreitol to break disulphide bridges. When the antigen is examined in the same way, but the reducing agent omitted to retain the disulphide bridges intact, a strong signal is given. This suggests the epitope is at least partly conformational. Furthermore, NCA is related to CEA, with a high degree of sequence homology, and has a GPI anchor, but does not react with PR1A3. Therefore the GPI is unlikely to be sufficient for the epitope.

EXAMPLE 2

Molecular Modelling and in vitro Mutagenesis

Figure 9:
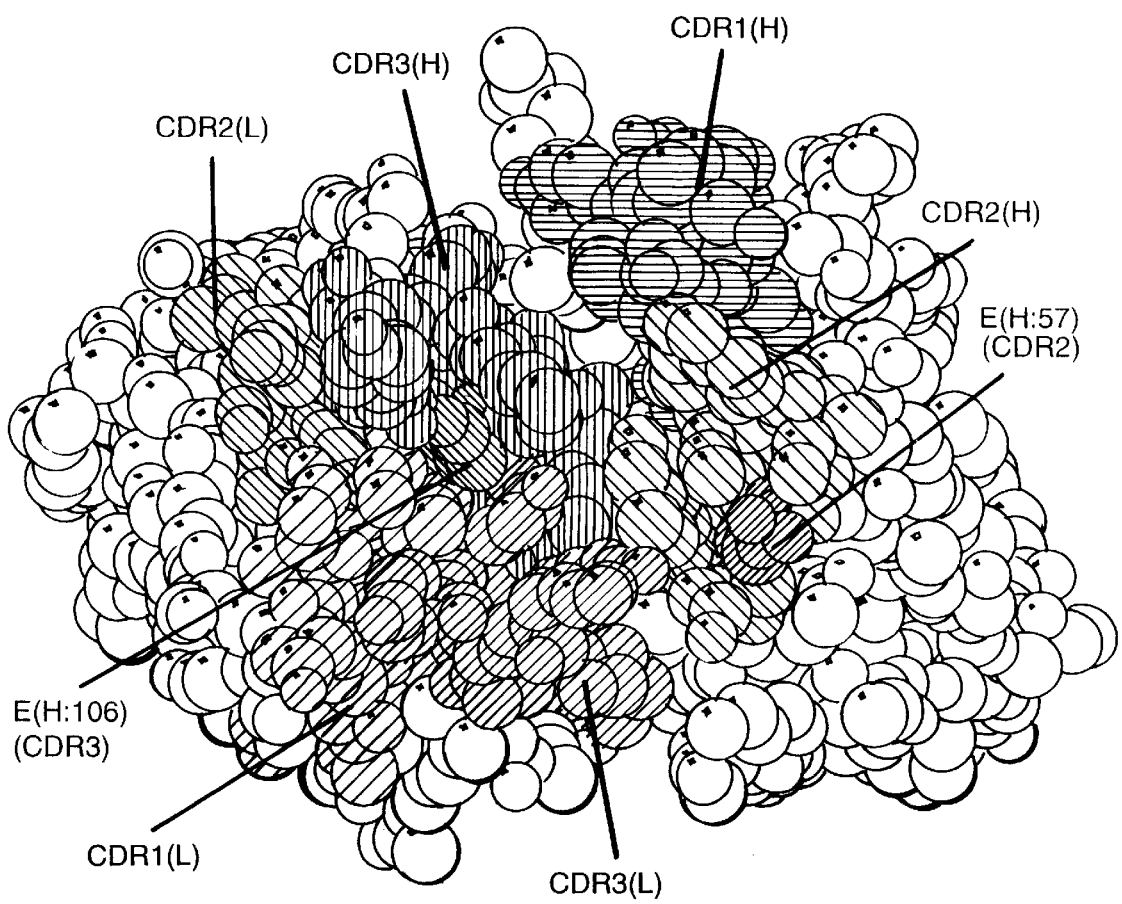
FIG. 9 shows a model of the V-domain of humanised antibody. The positions of the complementarity determining regions (CDRs) 1 to 3 of the light (L) and heavy (H) chains are shown. The two glutamic acid residues implicated in antigen recognition E(H:106)—position 106 of the heavy chain, and E(H:57)—position 57 of the heavy chain are marked.

Molecular models of the antibody PR1A3 demonstrate the presence of two unusual unpaired negative charges in the CDR region of the antibody. These charges may indicate the presence of complementary charges in the epitope recognised by the antibody (see FIGS. 9 and 10).

Analysis of the B3 domain of CEA and comparison with another family member, NCA, indicated that there were three residues carrying positive charges which could play an important role in the antibody antigen interaction. The residues were, lysines at positions 610 and 636 and arginine at position 514 in the CEA B3 domain. In order to assess the role of the individual charges in the epitope recognised by the antibody PR1A3, these residues were changed from lysine or arginine, to alanine. It is possible to alter these amino acids by changing the sequence of the DNA. The polymerase chain reaction may be used to introduce point mutations which are incorporated into one of the amplification primers. The fragment is then blunt-ended with Klenow fragment or digested with restriction endonucleases and ligated into the appropriate vector to allow the product to be sequenced. Alternatively, to introduce a mutation into the middle of a sequence, two fragments encompassing the mutation are annealed with each other and extended by mutually primed synthesis. The fragment may then be digested as before and ligated into an appropriate vector to be sequenced.

PCR may also be used to incorporate a phosphorylated oligonucleotide during amplication with Taq polymerase and Taq ligase (Michel, *BioTechniques* 16(3), 410–412).

Mutations may also be introduced by construction of a totally synthetic gene or portion of the gene.

The method which we used to introduce changes into the sequence was oligonucleotide directed mutagenesis by the method of Kunkel (1985) *Proc. Natl. Acad. Sci. USA* 82, 488–492).

The repetitive nature of CEA meant that in order to carry out the mutagenesis the B3 domain and downstream sequences of CEA had to be isolated from similar upstream sequences. This region was amplified with primers to introduce a ClaI site 5' and an XbaI site 3' and the fragment was cloned into pBluescriptII KS-. The plasmid was transformed into a dut⁻ung⁻ F' strain of *E. coli* (CJ236) which will produce plasmid with a number of uracil residues in place of thymine. Single stranded template was produced by superinfection with a helper phage M13 K07. A phosphorylated oligonucleotide containing the mutant sequence is annealed to the template and extended in the presence of T4 DNA polymerase and ligase to produce a double-stranded circular molecule. Introduction of this heteroduplex molecule into a wild-type (dut⁺ung⁺) strain resulted in degradation of the uracil containing wild-type strand and replication of the mutant strand. Colonies were isolated and the DNA sequenced to ensure that the mutant genotype was present. Mutations

| WILD-TYPE SEQUENCE | ATC | GCC | AAA | ATC | ACG | (SEQ ID No 21) |
|---|---|---|---|---|---|---|
| K1 MUTANT OLIGO | ATC | GCC | GCA | ATC | ACG | (SEQ ID No 22) |
| WILD-TYPE SEQUENCE | ATA | GTC | AAG | AGC | ATC | (SEQ ID No 23) |
| K2 MUTANT OLIGO | ATA | GTC | GCG | AGC | ATC | (SEQ ID No 24) |
| WILD-TYPE SEQUENCE | TCT | TGG | GGT | ATC | AAT | (SEQ ID No 25) |
| R1 MUTANT OLIGO | TCT | TGG | GCT | ATC | AAT | (SEQ ID No 26) |

After the mutant constructs were sequenced, these B3 domains were used to reconstitute the chimeric proteins consisting of residues 1–314 of BGP and residues 490–668 of CEA. These constructs have been shown to be positive for PR1A3 binding when transiently expressed in COS cells.

Figure 10:
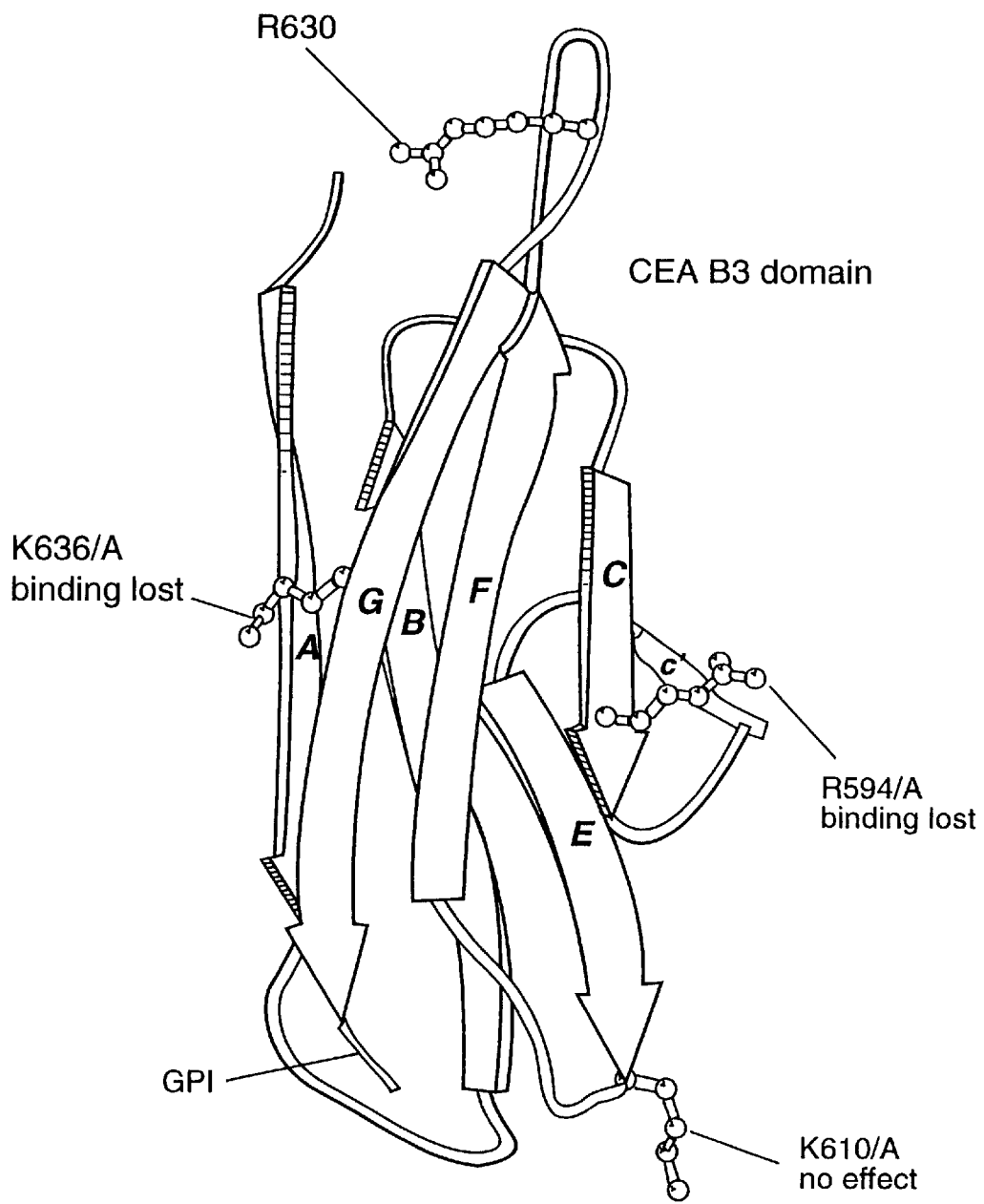
FIG. 10 shows a model of the B3 domain of CEA. The positions of the lysine and arginine residues are marked. In vitro mutagenesis of KG36 (lysine at position 636) and R594 (arginine position 594) destroys PR1A3 binding to the antigen.

After insertion into pCDM8 and expression in COS cells, immunofluorescence experiments demonstrated that the constructs carrying the K2 (lysine 636→alanine) and R3 (arginine 594→alanine) mutations were no longer recognised by PR1A3 whereas the K1 (lysine 610 alanine) mutation had no effect on binding (see FIG. 10). These results implicate the residues K2 and R3 in the epitope recognised by PR1A3.

EXAMPLE 3

Preparation and Properties of Monoclonal Antibodies Reactive Against CEA

Monoclonal antibodies reactive against CEA were prepared by the method of Richman & Bodmer (1987).

Tissues, cells, cell culture

Fresh samples of normal large intestine and colorectal tumours were used. These were snap-frozen in liquid nitrogen and stored at −70° C. Frozen samples of extra-colonic normal human adult and fetal tissues were used.

The colorectal carcinoma cell lines used originated from different tumours. HT29 colon carcinoma cell line (Fogh and Trempe, 1975) was maintained in medium RPM1 1640 containing 10% fetal calf serum (FCS) and 37° C. in 5% $CO_2$ in air at 100% humidity. LS174T, SW1222, SW48, SW620 and SW837 colorectal carcinoma cell lines (Tom et al., 1976; Leibovitz et al., 1976) were maintained in Dulbecco's modified Eagle's medium containing 10% FCS at 37° C. in 10% $CO_2$ in air at 100% humidity.

P3/NS1/1-Ag-4-1 (NS1) is an 8-azaguanine-resistant BALB/c myeloma cell line. This was maintained in RPMI 1640 with 10% FCS and $2 \times 10^{-5}$M 6-thioguanine.

Hybridomas produced in this study were initially cultured in RPMI 1640 with 20% FCS, $10^{-4}$M hypoxanthine, $1.6 \times 10^{-5}$M thymidine and $10^{-5}$M methotrexate (HAT). After cloning, hybridoma cells were weaned off HAT and maintained in RMPI 1640 with 10% FCS.

Immunizing materials

BALB/c mice were immunized with 4 different preparations.

1. Normal colorectal mucosal scrapings. Samples of normal large intestine were pinned onto a cork board. After thorough rinsing (10 times) in cold, sterile phosphate-buffered saline-A, pH 7.4 (PBS-A), the mucosa was dissected from the muscularis mucosae by scraping with a scalpel. Mucosal scraping were snap-frozen in liquid nitrogen and mechanically vibrated to a powder in a polypropylene vial containing a tungsten ballbearing. This material was emulsified in 0.2 ml complete Freund's adjuvant and 0.2 ml PBS-A. Animals received 0.2 g wet tissue in 0.4 ml emulsion per inoculation.

2. Crude membrane preparations from normal colorectal epithelium. Fresh normal colorectal mucosal scrapings were prepared as above. One gram of wet tissue was used for each membrane preparation. Tissue samples were thawed and Dounce-homogenized in 10 ml sucrose buffer containing dithiothreitol (DTT) (250 mM sucrose-RNase free: 50 mM triethanolamine-HCl pH 7.5; 60 mM $MgCl_2$; 2 mM DTT). Following centrifugation at 40,000 g for 15 min, the nuclear and mitochondrial pellet was discarded. The supernatant was then centrifuged for a further 30 min at 20,000 g. The microsomal pellet was retained and resuspended in 40% sucrose in 10 mM Tris HCl pH 7.4. The sucrose solution was adjusted to obtain a refractometer reading of 1.392–5, overlaid with 25% sucrose in 10 mM Tris HCl pH 7.4 (refractometer reading 1.375) and the sucrose gradient was centrifuged at 4° C. for 15 hr at 65,000 g. Membranes were recovered from the interface and washed twice in 10 mM Tris pH 7.4; protein content was estimated by the method of Lowry et al. (1951). One gram of wet tissue yielded approximately 1 mg of membrane protein. The membranes were suspended in PBS-A and complete Freund's adjuvant for injection. Animals received 0.4 ml emulsion per inoculation.

3. H729 colon carcinoma cell line. Animals received $2 \times 10^6$ live trypsinized cells suspended in 0.4 ml PBS-A per inoculation.

4. Epitope as immunogen. The immunogen is a cell carrying hybrid BGP-CEA B3-GPI protein or a cell transfected with CEA cDNA or cosmid. A mouse L cell transfected with CEA gene is used to immunise an appropriate mouse strain to give antibodies to CEA. Human tumour cells expressing CEA can also be used.

Immunization and production of hybridomas

Three fusions were carried out using spleens from BALB/c mice immunized by intraperitoneal inoculations according to the following protocol. In fusions 1 and 2, mice were immunized and boosted with mucosal scrapings and membrane preparations of normal colorectal epithelium (see "Immunizing materials" above). In fusion 3, initial immunization was with membrane preparations of normal colon and subsequent booster inoculations were with HT29 colon carcinoma cells. Animals received intraperitoneal injections of these materials 6 weeks, 2 weeks and 4 days prior to each fusion. In each case, the spleen was removed aseptically; a single-cell suspension was prepared mechanically and the spleen cells were fused with $10^8$ NSI myeloma cells using 50% polyethyleneglycol 4,000 (Merck) in RPMI 1640. The cells were plated into 24- or 96-well plates (Linbro, Flow, Irvine, Scotland) containing RPMI 1640 with HAT plus 20%

FCS and mouse spleen cells as a feeder layer. The plates were incubated at 37° C. in 5% $CO_2$ in air at 100% humidity. Hybridomas were generally visible microscopically at 14–21 days; initial screening to identify interesting colonies was performed prior to cloning. These colonies were cloned twice by picking single cells with a drawn-out Pasteur pipette, transferring them to individual wells of 96-well Microtitre plates containing mouse spleen cell feeders overlaid with 2 ml RPMI 1640, HAT and 20% FCS, and cultured at 37° C. in 5% $CO_2$ in air in 100% humidity.

Screening assay for antibody production

Screening for antibody production from all fusions was performed on tissue sections using an indirect immunoperoxidase technique. Cryostat sections (6 μm thickness) were cut from snap-frozen cubes of normal large intestine. The sections were picked up on 10-well multitest slides (C. A. Hendley-Essex, England) precoated with 0.1% poly-1-lysine and allowed to dry in air for 30 min at room temperature. The sections were fixed in acetone for 15 min. Individual wells were incubated with 20 μl unconcentrated hybridoma tissue culture supernatant for 30 min at room temperature in a humid chamber. Slides were washed twice in Tris-buffered saline (TBS) pH 7.6 (Tris, 605 mg, NaCl, 8 g in 1 l distilled water) before incubation for 30 min at room temperature with peroxidase-conjugated rabbit anti-mouse immunoglobulin (DAKO, Copenhagen, Denmark) diluted 1:50 in TBS containing 5% normal human serum. The slides were washed again in TBS and then flooded with freshly prepared filtered solution of diaminobenzidine (Sigma. St. Louis, Mo.) 5 mg in 10 ml Tris HCl pH 7.6 containing 0.03% hydrogen peroxide. The peroxidase substrate reaction was stopped after 5 min by washing in tap water and the slides were counterstained with Heyer's haematoxylin, dehydrated in alcohol and mounted in DPX (BDH, Poole, UK).

Immunohistochemical methods

1. Indirect immunoperoxidase staining of formalin-fixed tissue. To determine the reactivity of the MAbs with formalin-fixed, paraffin-embedded tissues, samples of normal large intestine were fixed in either (a) 10% neutral buffered formalin or (b) acid formalin (2% acetic acid in 10% formalin) for 2 hr. After routine processing 3–4 μm sections were stained by the indirect peroxidase technique as described above (see "Screening"). Prior to staining, endogenous peroxidase activity was blocked by incubating the sections for 10 min in a humid chamber at room temperature with a freshly prepared solution of 0.5% hydrogen peroxide in methanol. After washing in tap water, slides were treated in one of 3 ways irrespective of the type of fixative used. (i) Stained directly; (ii) Digested in trypsin. For digestion slides were warmed at 37° C. in distilled water and transferred to a freshly prepared solution of 0.1% trypsin (Sigma, type II), 0.1% $CaCl_2$, pH 7.8 with NaOH for periods of 5–40 min (iii) Digested with other protease solutions. Warmed slides were transferred to a solution of protease (Sigma, type IV), 0.025% in TBS pH 7.6 for 5–15 min.

In (i) and (ii) above, enzyme reactions were stopped with cold running water. After thorough washing in water and TBS the digested sections were stained by the indirect immunoperoxidase technique.

2. Indirect immunoperoxidase staining of frozen tissue sections. Frozen sections of normal large intestine, other normal tissue and colorectal tumours were prepared as described above (see "Screening"). They were picked up on 4-well multitest slides (C. A. Hendly-Essex) and stained. They were not enzyme-digested and endogenous peroxidase activity was not blocked. All tissues were counterstained in Meyer's haematoxylin, dehydrated in a graded alcohol series, cleared in xylene and mounted in DPX.

3. Immunofluorescence of frozen sections. Frozen sections of both normal colorectal tissue and some tumours were also examined by indirect immunofluorescence. After fixing in acetone for 15 min, sections were washed in phosphate-buffered saline (PBS). Sections were then incubated with 20 μl unconcentrated hybridoma supernatant for 30 min in a humid chamber, washed 3 times in PBS and incubated for a further 30 min with fluorescein-conjugated rabbit anti-mouse IgG (DAKO) diluted 1:40 in PBS. After 3 further washes in PBS and a final wash in distilled water, the sections were mounted in Gelvato 20/30 (Monsanto, Springfield, Mass.) and viewed on a Leitz Orthoplan microscope with epifluorescence attachment.

4. Immunocytochemical examination of cell lines. Cells from the carcinoma lines were grown on glass slides. They were washed 3 times in PBS-A and then stained either live or after fixation in acetone for 10 min.

5. Controls. Immunohistochemical staining was controlled by the use of nonhybridoma tissue culture medium (RPMI 1640 with 10% FCS) as the primary layer. In addition, for immunoperoxidase staining the second antibody-enzyme conjugate and diaminobenzidine solution were also used individually. For immunofluorescence the FITC-conjugated rabbit anti-mouse IgG was used alone. Non-specific staining by these reagents was not observed.

Assessment of colorectal tumours

The colorectal adenocarcinomas were graded histologically by the criteria of Blenkinsopp et al. (1981) using sections stained with haematoxylin and eosin. For each antibody tumours were assessed as "negative" (no reactive cells), "heterogeneous" (some reactive cells) or "positive" (all cells reactive). Variations in the staining intensity between different cells of the same tumour or between tumour cells and the adjacent normal epithelium were sometimes seen but not quantitated.

Antibodies are screened by indirect immunofluorescent assays using CEA-positive cells air-dried and acetone-fixed on to cover slips. Also, whole cells or tissue sections carrying CEA are used and detection is by ELISA or radioimmunoassay (RIA).

Antibodies which are positive for CEA-expressing cell lines, negative for BGP- and NCA-expressing cell lines, and negative for BGP-CEA B3-expressing and BGP-CEA B3-BGPTM-expressing cell lines comprise antibodies of the invention.

EXAMPLE 4

Preparation of Monospecific Polyclonal Antibodies Reactive Against CEA

To prepare monospecific polyclonal antibodies reactive against CEA a suitable animal (rabbit, goat or the like) is immunized with hybrid BGP-CEA B3-GPI. The antisera so produced is then absorbed with purified BGP or cells expressing BGP to remove BGP-reactive antibodies and to leave the CEA reactive antibodies of the invention.

EXAMPLE 5

Radioimmunoscintigraphy (RIS) of Colorectal Cancer

Antibodies are used in RIS as described by Granowska et al (1989) in *Nuclear Medicine, trends and possibilities in nuclear medicine,* pp. 531–534 Schmidt & Buraggi (eds.), Schattauer, N.Y. A monoclonal antibody obtained by the method of Example 2 is labelled with indium-111 using the bifunctional chelate method of Hnatovich et al (1987). Imaging is undertaken using a Siemans 75 tube digitrac rotating gamma camera set with a medium energy parallel hole 'gallium' collimator and linked to a Nodecrest V77 computer. The camera is peaked to the two energies of In-111 with 15% and 20% windows and the counts are summed. Images are displayed on transparent film and in colour on the visual display unit of the computer.

Patients with primary or suspected recurrent colorectal cancer are selected by the surgeons and presented for RIS. The study is approved by the Administration of Radioactive Substances Advisory Committee of the Department of Health. Signed informed consent is obtained from each patient. Patients with a history of allergy to foreign proteins or with a positive skin test to the antibody are to be excluded. Patients with low rectal tumours were studied using multiple per rectal submucosal injection of antibody to undertake lymphoscintigraphy.

After the injection of 2–3 mCi (80–120 MBq) of a known amount of activity, imaging was performed immediately, sometimes at 4 hours, at 24 hours with emission tomography, and at 48, 72 or 96 hours. Anterior and posterior views of the lower chest and upper abdomen, and lower abdomen and pelvis are obtained, together with images of six radioactive marker sources set on the bone land-marks to check repositioning of the patient and the image at each time point. Gamma camera images are also made of the excised surgical specimen. The histological staging and grading of the tumour is undertaken. Specimens of the tumour, nearby mucosa and lymph nodes known to be involved or not involved with tumour are selected and counted, together with standards and appropriate background samples. Serial blood and urine samples are also assayed.

Blood clearance at 24 hours averages 51%; at 48 hours 33% and at 72 hours 27% of the injected dose taking the 5 minute sample volume as 100 percent. Urine output is less than 3%.

Images of primary and recurrent colorectal cancer are of high quality. Tumour sites are clearly identified in the abdomen and pelvis often as early as 4 hours. Liver metastases are identified as focal defects on the early images which took up activity progressively with time. There is appreciably less normal bowel uptake than we are accustomed to with In-111 anti CEA (that is, anti-CEA antibodies that do not recognise the epitope recognised by PR1A3). Marrow and liver uptakes are similar. No false positive or false negative results are obtained. Single photon emission tomography is of no particular benefit since the planar images were so good.

Imaging of a surgical specimens shows that tumours and polyps have high uptake and that, unlike with other anti CEA antibodies (that do not recognise the epitope recognised by PR1A3) normal nodes are not visualised. The tumour to mucosa ratios are high ranging up to 47:1. Poorly differentiated tumours take up the antibody reasonably well and, on average, better than with In-111 anti CEA (that do not recognise the epitope recognised by PR1A3).

EXAMPLE 6

Humanising a Mouse Monoclonal Antibody (CDR Grafting)

Complementary DNAs (cDNAs) encoding the variable regions of the monoclonal antibody were cloned and sequenced. Primers used for PCR cloning of the heavy chain V-region were from Orlandi et al (1989) and for the light chain V-region were from Jones & Bendig (1991). In each instance two sequences were given, one each for the parental NS1 light and heavy chains and unique sequences for a heavy chain and a light chain.

To confirm the specificity of the unique sequences they were expressed as a human-mouse chimaeric antibody where the mouse antibody V-regions were fused to human constant regions. The mouse antibody $V_H$-region clone was linked to a cDNA clone of the C-regions of the human $IgG_1$ heavy chain NEWM (Kabat et al (1991) supra) by PCR techniques (see FIG. 1). The mouse antibody $V_L$-region was linked to a cDNA clone of the human kappa light chain REI (Kabat et al (1991) supra) by PCR techniques (see FIG. 2).

The NEWM sequence is disclosed in Poljak et al (1977) *Biochemistry* 16, 3412–3420 and the REI sequence is disclosed in Palm & Hilschmann (1973) *Z. Physiol. Chem.* 354, 1651–1654 both incorporated herein by reference.

The chimaeric light and heavy chains were then inserted into the expression vector pCDM8 and the two plasmids co-transfected into COS cells. After eight days of culture antibody levels of approximately 1 μg/ml were determined in a human IgG Fc specific ELISA and the chimaeric antibody gave a positive immunofluorescent staining on MKN45 cells, a human gastric carcinoma cell line that carries the determinant identified by PR1A3.

The DNA sequences of the V-regions were used to design humanised antibody. Analysis of the database allowed the selection of a human antibody with similarity to the mouse antibody (about 75% homology). This human antibody sequence was used as the template to design a humanised antibody sequence which was constructed from overlapping oligonucleotides and PCR and then linked to the cDNA of NEWM heavy chain.

The murine light chain had a homology of 70% to the human light chain. The light chain was then used as the template to construct humanised PR1A3 light chain using oligonucleotides and PCR by the method of Lewis & Crowe (1991).

Methods

Figure 6:
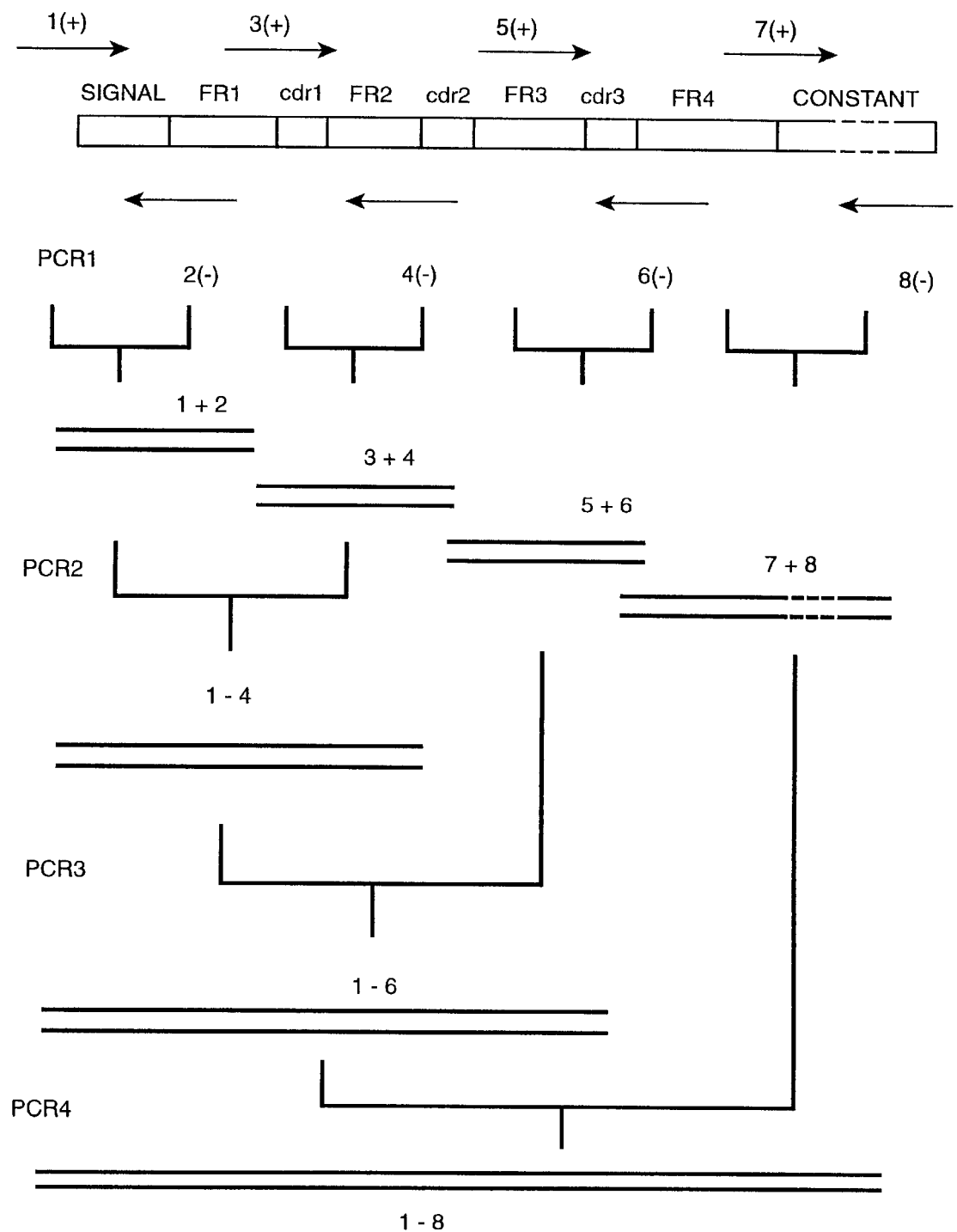
FIG. 6 shows the construction of a humanised heavy chain. FR indicates framework regions; CDR indicates complementarity determining regions; = indicates double stranded DNA encoding humanised heavy chain; and → indicates synthetic oligonucleotides, showing direction 5'-3', used as primers for overlapping PCR.

Heavy Chain (see FIG. 6)

Synthetic oligonucleotides, 1–6, code for the variable region of the heavy chain of the monoclonal antibody. These oligonucleotides (90mers) coded alternatively for the sense or the antisense strand of DNA, with 12 base pair overlaps between each sequential oligonucleotide. Primer dimer formation between pairs of oligonucleotides occurs, followed by PCR amplification.

The constant region was primed from a human heavy chain sequence contained within a plasmid. Incorporated into these primers was a 5' overlap with the 3' end of the variable region and a cloning site at the extreme 3' end of the gene.

PCR Conditions

```
95° C./1 min    ← add Taq DNA polymerase
60° C./2 min  ⎫
72° C./2 min  ⎬  ×30
95° C./1 min  ⎪
60° C./2 min  ⎭
72° C./7 min
```

Figure 7:
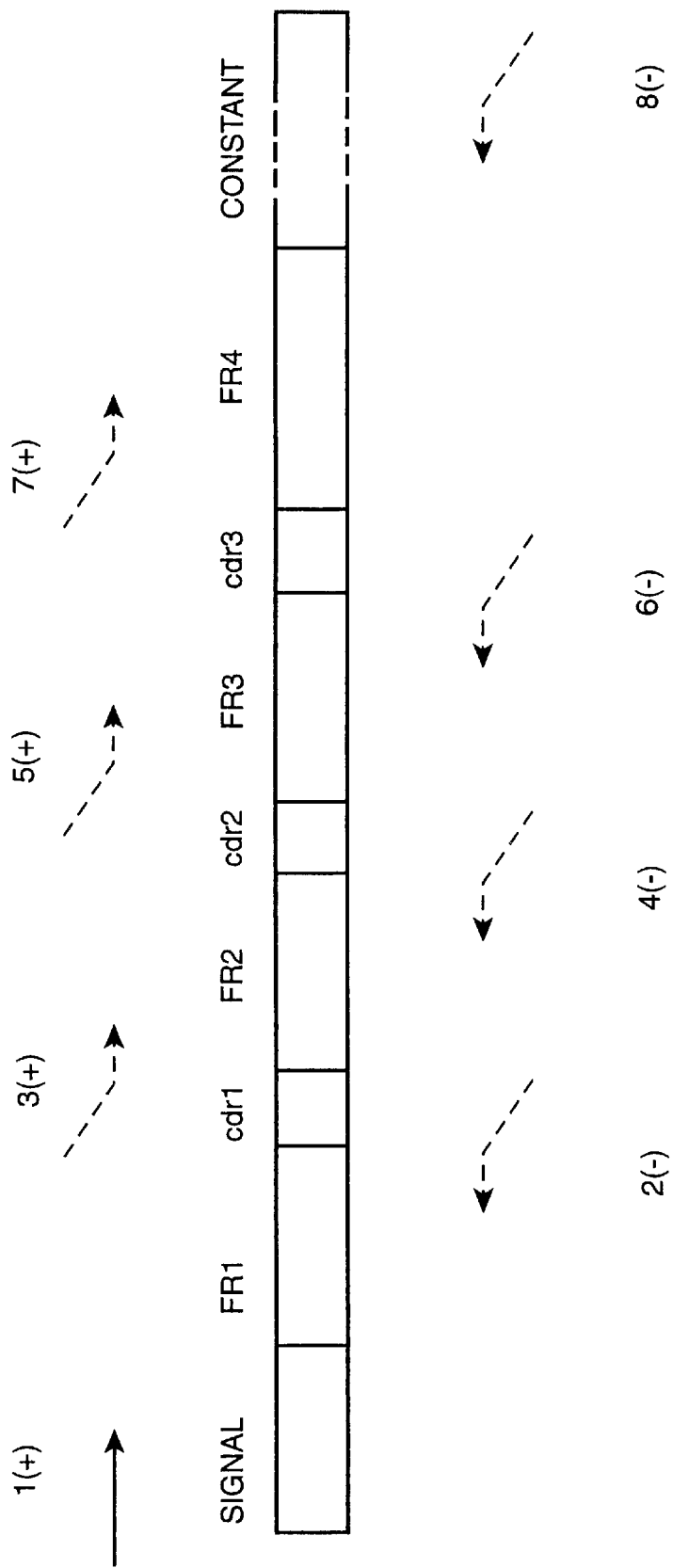
FIG. 7 shows the construction of a humanised light chain. FR indicates framework regions; CDR indicates complementarity determining regions; =indicates double stranded DNA encoding humanised heavy chain; and → indicates synthetic oligonucleotides, showing direction 5'-3', used as primers for overlapping PCR.

Light Chain (see FIG. 7)

The light chain was constructed in a similar manner to the heavy chain. Primers 1+2, 3+4, 5+6, 7+8 were PCR-amplified to produce overlapping fragments. The programme used was the same as for the heavy chain. The fragments were then joined using the following PCR programme.

Initially only the fragments are added.

| Initially only the fragments are added. |
|---|
| 93° C./1.5 min ⎫ |
| 37° C./1.0 min ⎬ ×7 |
| 72° C./2.0 min ⎭ |
| Outside primers are added. |
| 93° C./1.5 min ⎫ |
| 37° C./1.0 min ⎬ ×25 |
| 72° C./2.0 min ⎭ |
| 93° C./1.5 min |
| 37° C./1.0 min |
| 72° C./10.0 min |

The template for this construct was a human light chain sequence contained within a plasmid. Primers (20–30 mers) were designed to have a 3' region which was complementary to the human framework and a foreign 5' region (either restriction enzyme sites or partial monoclonal antibody CDRs). The frameworks were amplified and the 5' foreign sequences were incorporated during this amplification. The individual fragments overlaps at the ends and were joined by overlapping PCR to form the complete gene.

Light and heavy chains have been inserted into the expression vector pCDM8 and antibody is being expressed in COS cells and its binding activity to MKN45 cells confirmed by immunofluorescence.

The V-regions of PR1A3 have been modelled using co-ordinates from structures of antibodies known from X-ray crystallographic studies. The complementarity determining regions (CDRs) were fitted to the framework structures using the canonical loop structures derived from Chothia et al (1992). Prominent features of the model include an additional residue, a tyrosine, in CDR3 of the light chain, and two glutamic acid residues, one in CDR2 of the heavy chain, and the other in CDR3 of the heavy chain. The two glutamic acids are unusual in that they are unpaired charges, but the additional tyrosine in CDR3-L causes this loop to kink and allows salt bridges to form between the two tyrosines in the CDR3-L loop and the unpaired glutamic acids of VH to stabilise the structure. The presence of these features is strongly suggestive that they are key to antigen recognition and that the epitope is positively charged.

Sequencing the V-region of the mouse PR1A3 heavy chains has consistently given a choice of two residues for the first amino acid of CDR1-H, both valine and glutamine have been found. Chimaeric antibodies of both isotypes are equally active in immunofluorescent studies with MKN45 cells and modelling allows both amino acids to be positioned with no constraints being imposed on the structure.

EXAMPLE 7

Acetone Fixation of Cells and Determination of Binding

Cell suspensions, approximately $10^5$ cells/ml in phosphate-buffered saline (PBS), were dropped onto microscope slides and allowed to dry, then immersed in acetone for 10 minutes and rinsed in PBS. Alternatively, coverslips were placed into a Petri dish containing culture medium such as RPMI 1640 containing 10% foetal calf serum, and cells seeded on to the coverslips. The Petri dishes were then incubated for between 48 and 72 hours at 37° C., and then were removed from the Petri dish, rinsed in PBS, immersed in acetone 10 minutes and then rinsed in PBS. The slides or coverslips were then incubated with the appropriate test antibody and washed. The test antibody either bound to or did not bind to the cell.

In order to detect binding of the test antibody, an anti-species antibody, labelled with fluorescein isothiocyanate (FITC), is added and then the cells washed. Binding is determined by measuring the fluorescence.

When mouse IgG is the test antibody FITC-conjugated sheep anti-mouse antibody (Sigma Chemical Co, Poole, Dorset, UK) is used as the probe.

The cells used for binding studies are the colon carcinoma cell line HT-29 (ATCC HTB 38); COS-7 cells transfected with CEA cDNA; and COS-7 cells transfected with any of the DNA chimaeric constructs described in Example 1.

Transfection of the COS-7 cells is by electroporation.

Electroporation: 200 μg of plasmid DNA were mixed with 0.8 ml of cells in PBS, at a concentration of $10^7$–$10^8$ cells/ml. Cells were pulsed with 1 kv, 25 μFD capacitance using a Bio-Rod Gene Pulser. Cells were then placed on ice for at least 10 minutes before transfer to culture medium. Following overnight incubation at 37° C. fresh medium was added to the cells.

EXAMPLE 8

Humanising a Mouse Monoclonal Antibody (Chimaeric Fusions)

The variable region of the murine monoclonal antibody was amplified by PCR using primers which added a HindIII restriction site to the 5' end of the sequence and the 3' end was designed to have a region of overlap with the 5' end of the constant domain of the kappa chain of the human antibody REI. This was amplified using standard amplification procedures (95° C. for 1 minute followed by 30 cycles of 95° C. for 1 minute, 60° C. for 2 minutes and 72° C. for 2 minutes with a final 72° C. for 10 minutes). The REI kappa constant fragment was amplified under the same conditions, with the primers adding a 5' overlap with the 3' end of the monoclonal antibody kappa variable and a 3' XbaI site. These fragments were joined and extended by mutually primed synthesis to produce a sequence containing the variable region of the kappa chain of the murine monoclonal antibody and the constant domain from the kappa chain of the human antibody REI. PCR condition were 7 rounds of amplification, in a reaction containing both fragments, of 95° C. for 2 minutes and 72° C. for 4 minutes after which the outside primers were added and subjected to standard amplification procedures.

The heavy chain was constructed in a similar manner using the variable region of the heavy chain of the murine monoclonal antibody and the constant domains from the human heavy chain of NEWM.

These fragments were removed by restriction endonuclease digestion with HindIII and XbaI. They were placed independently into the vectors pCDM8 and co-transfected into COS cells. The chimeric antibody was secreted into the medium and when tested by immunofluorescence against CEA expressed on the surface of MKN45 cells, exhibited all the characteristics of the construct which was murine in origin.

REFERENCES

Bates et al (1992) *FEBS Lett* 301, 207–214.
Blenlinsopp et al (1981) *J. Clin. Path.* 34, 509–513.
Chothia et al (1992) *J. Mol. Biol.* 227, 799–817.
Clackson et al (1991) *Nature* 352, 624–628.
Ferguson (1992) *Biochem. Soc. Trans.* 20, 243–256.
Fogh & Trempe (1975) "New human tumour cell lines" in J. Fogh (ed.), *Human tumour cells in vitro*, pp. 115–141, Plenum Press, New York.
Gram et al (1991) *Proc. Natl. Acad. Sci. USA* 89, 3376–3580.
Granowska et al (1989) *Int. J. Colorect. Dis.* 4, 9714 108.
Granowska et al (1990) *Br. J. Cancer*, 62 (Suppl X), 30–33.
Hnatowich et al (1983) *Science* 220, 613–615.
Jones & Bendig (1991) *Bio/Technology* 9, 88–89.
Leibovitz et al (1976) *Cancer Res.* 36, 4562–4569.
Lewis & Crowe (1991) *Gene* 101, 297–302.
Lowry et al (1951) *J. Biol. Chem.* 193, 265–275.
McCafferty et al (1990) *Nature* 348, 552–554.
Orlandi et al (1989) *Proc. Natl. Acad. Sci. USA* 86, 3833–3837.
Richman & Bodmer (1987) *Int. J. Cancer* 39, 317–328.
Salvatore et al (1989) *Int. J. Appl. Instrum. B* 16, 103–104.
Thompson & Zimmermann (1988) *Tumour Biol.* 9, 63–83.
Thompson et al (1991) *J. Clin. Lab. Analysis* 5, 344–366.
Tom et al (1976) In vitro 12, 180.

---

We claim:

1. A molecule which (i) binds membrane-bound human carcinoembryonic antigen, and (ii) binds a hybrid polypeptide consisting of residues 1 to 314 of human biliary glycoprotein (SEQ ID NO: 32) and joined (N-C) to residues 490 to C-terminus of human carcino embryonic antigen (SEQ ID NO: 36), but (iii) does not bind to human biliary glycoprotein and (iv) does not bind a hybrid polypeptide consisting of residues 1 to 314 of human biliary glycoprotein joined (N-C) to residues 490 to 643 of human carcino embryonic antigen which is soluble and is secreted from a COS cell, but excluding an intact mouse monoclonal antibody comprising an $IgG_1$ group IIA heavy chain and a kappa group V light chain wherein in the said intact mouse monoclonal antibody the sequence of the $V_H$ chain is

QVKLQQSGPELKKPGETVKISCKASGYTFTVFGMNW (SEQ ID NO: 1)

VKQAPGKGLKWMGWINTKTGEATYVEEFKGRFAFSLETSATTAYLQINNLK

NEDTAKYFCARWDFYDYVEAMDYWGQGTTVTVSS, or wherein in the said intact mouse monoclonal antibody the sequence of the $V_H$ chain is as given immediately above but the first amino acid residue of the $V_H$ CDR1 is glutamine and in either case the sequence in the said intact monoclonal antibody of the $V_L$ chain is

GDIVMTQSQRFMSTSVGDRVSVTCKASQNVGTNVAW (SEQ ID NO: 2)

YQQKPGQSPKALIYSASYRYSGVPDRFTGSGSGTDFTLTISNVQSEDLAEY

FCHQYYTYPLFTFGSGTKLEMKR.

2. A molecule according to claim 1 wherein the molecule is a monospecific antibody.

3. A molecule according to claim 1 which is an antibody comprising a human framework region and at least the complementarity determining regions of the $V_H$ chain and $V_L$ chain as defined in claim 1 wherein for the $V_H$ chain CDR1 is VFGMN (SEQ ID NO: 3), CDR2 is WINTKTGEATYVEEFKG (SEQ ID NO: 4) AND CDR3 is WDFYDYVEAMDY (SEQ ID NO: 5) and for the $V_L$ chain CDR1 is KASQNVGTNVA (SEQ ID NO: 6), CDR2 is SASYRYS (SEQ ID NO: 7) and CDR3 is HQYYTYPLFT (SEQ ID NO: 8).

4. A molecule according to claim 3 wherein the antibody is a monoclonal antibody.

5. A molecule according to claim 1 further comprising a directly or indirectly cytotoxic moiety.

6. A molecule according to claim 1 further comprising a readily-detectable label.

7. A molecule according to claim 1 for use in medicine.

8. A medicament for diagnosing or treating colorectal carcinoma comprising a molecule according to claim 1.

9. A method for diagnosing or treating colorectal carcinoma comprising administering to a person a composition comprising the molecule according to claim 1 and, optionally, a non-pyrogenic diluent.

10. A process for making a monospecific antibody as defined in claim 2, the process comprising screening a pool of antibodies to select those monospecific antibodies which bind (i) human carcinoembryonic antigen, (ii) bind a hybrid polypeptide consisting of residues 1 to 314 of human biliary glycoprotein joined (N-C) to residues 490 to 668 of human carcinoembryonic antigen, but (iii) do not bind to human biliary glycoprotein.

11. A process according to claim 10 wherein the monospecific antibody is a monoclonal antibody and the pool of antibodies is a pool of monoclonal antibodies.

12. A process according to claim 10 wherein the antibodies within the pool comprise antibodies produced by recombinant DNA methods.

13. A process according to claim 12 wherein the binding sites of the antibodies are displayed on the surface of a replicating vector.

14. A process according to claim 13 wherein the replicating vector is a bacteriophage.

15. A monospecific antibody obtainable by the process of claim 10 but excluding an intact mouse monoclonal antibody comprising an $IgG_1$ group IIA heavy chain and a kappa group V light chain wherein in the said intact mouse monoclonal antibody the sequence of the $V_H$ chain is

QVKLQQSGPELKKPGETVKISCKASGYTFTVFGMNW (SEQ ID NO: 1)

VKQAPGKGLKWMGWINTKTGEATYVEEFKGRFAFSLETSATTAYLQINNLK

NEDTAKYFCARWDFYDYVEAMDYWGQGTTVTVSS, or wherein in the said intact mouse monoclonal antibody the sequence of the $V_H$ chain is as given immediately above but the first amino acid residue of the $V_H$ CDR1 is glutamine; and in either case the sequence in the said intact monoclonal antibody of the $V_L$ chain is

GDIVMTQSQRFMSTSVGDRVSVTCKASQNVGTNVAW (SEQ ID NO: 2)

YQQKPGQSPKALIYSASYRYSGVPDRFTGSGSGTDFTLTISNVQSEDLAEY

FCHQYYTYPLFTFGSGTKLEMKR.

16. A hybrid polypeptide consisting of residues 1 to 314 of human biliary glycoprotein joined (N-C) to residues 490 to 668 of human carcinoembryonic antigen.

17. A hybrid polypeptide consisting of residues 1 to 314 of human biliary glycoprotein joined (N-C) to residues 490 to 643 of human carcinoembryonic antigen.

18. A hybrid polypeptide consisting of residues 1 to 314 of human biliary glycoprotein joined (N-C) to residues 490 to 644 of human carcinoembryonic antigen joined (N-C) to residues 391 to 430 of human biliary glycoprotein.

19. A hybrid polypeptide consisting of residues 1 to 314 of human biliary glycoprotein joined (N-C) to residues 490 to 642 of human carcinoembryonic antigen joined (N-C) to residues 387 to 430 of human biliary glycoprotein.

* * * * *

UNITED STATES PATENT AND TRADEMARK OFFICE
CERTIFICATE OF CORRECTION

PATENT NO. : 5,965,710
DATED : October 12, 1999
INVENTOR(S) : Bodmer et al.

It is certified that error appears in the above-identified patent and that said Letters Patent is hereby corrected as shown below:

Item [57] Abstract,
Line 18, delete "GPDRF" and insert --GVPDRF--.
Figure 1, fifth to the last line, delete "VEAND" and insert --VEAMD--.

Column 2,
Line 21, delete "QINNLKNEDTAKYFCARWDFYDYEAMYWGQGTTVTVS" and insert --QINNLKNEDTAKYFCARWDFYDYVEAMDYGWGQGTTVTVS--.

Column 13,
Line 67, delete "2x10$^{-5M}$" and insert --2x10$^{-5}$M--.

Column 14,
Line 2, delete "10$^{-4M}$" and insert --2x10$^{-4}$M--; and
Line 3, delete "10$^{-5M}$" and insert --10$^{-5}$M--, and delete "10$^{-5M}$" and insert --10$^{-5}$M--.

Column 20,
Line 24, delete "$_{10}$$^{7}$" and insert --10$^{7}$--.

Column 21,
Line 4, delete "Blenlinsopp" and insert --Blenkinsopp--;
Line 9, delete "*pp.*" and insert --pp.--; and
Line 13, delete "9714" and insert --97- --.

Signed and Sealed this

Seventeenth Day of July, 2001

Attest:

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
      (A) LENGTH: 121 amino acids
      (B) TYPE: amino acid
      (C) STRANDEDNESS: single
      (D) TOPOLOGY: linear (ii) MOLECULE TYPE: peptide (iii) HYPOTHETICAL: NO (v) FRAGMENT TYPE: internal (vi) ORIGINAL SOURCE:
      (A) ORGANISM: VH chain (xi) SEQUENCE DESCRIPTION: SEQ ID NO: 1:

```
Gln Val Lys Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Val Phe
            20                  25                  30

Gly Met Asn Trp Val Lys Gln Ala Pro Gly Lys Gly Leu Lys Trp Met
        35                  40                  45

Gly Trp Ile Asn Thr Lys Thr Gly Glu Ala Thr Tyr Val Glu Glu Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Lys Tyr Phe Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

(2) INFORMATION FOR SEQ ID NO: 2:

(i) SEQUENCE CHARACTERISTICS:
      (A) LENGTH: 110 amino acids
      (B) TYPE: amino acid
      (C) STRANDEDNESS: single
      (D) TOPOLOGY: linear (ii) MOLECULE TYPE: peptide

```
       (iii) HYPOTHETICAL: NO (v) FRAGMENT TYPE: internal (vi) ORIGINAL SOURCE:
            (A) ORGANISM: VL chain (xi) SEQUENCE DESCRIPTION: SEQ ID NO: 2:

Gly Asp Ile Val Met Thr Gln Ser Gln Arg Phe Met Ser Thr Ser Val
1               5                  10                  15

Gly Asp Arg Val Ser Val Thr Cys Lys Ala Ser Gln Asn Val Gly Thr
                20                  25                  30

Asn Val Ala Trp Tyr Gln Gln Lys Pro Gly Gln Ser Pro Lys Ala Leu
            35                  40                  45

Ile Tyr Ser Ala Ser Tyr Arg Tyr Ser Gly Val Pro Asp Arg Phe Thr
    50                  55                  60

Gly Ser Gly Ser Gly Thr Asp Phe Thr Leu Thr Ile Ser Asn Val Gln
65                  70                  75                  80

Ser Glu Asp Leu Ala Glu Tyr Phe Cys His Gln Tyr Tyr Thr Tyr Pro
                85                  90                  95

Leu Phe Thr Phe Gly Ser Gly Thr Lys Leu Glu Met Lys Arg
                100                 105                 110

(2) INFORMATION FOR SEQ ID NO: 3:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: VH chain CDR1

(xi) SEQUENCE DESCRIPTION: SEQ ID NO: 3:

Val Phe Gly Met Asn
1               5

(2) INFORMATION FOR SEQ ID NO: 4:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: VH CDR2

(xi) SEQUENCE DESCRIPTION: SEQ ID NO: 4:

Trp Ile Asn Thr Lys Thr Gly Glu Ala Thr Tyr Val Glu Glu Phe Lys
1               5                  10                  15

Gly (2) INFORMATION FOR SEQ ID NO: 5:
```

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: VH chain CDR3

(xi) SEQUENCE DESCRIPTION: SEQ ID NO: 5:

Trp Asp Phe Tyr Asp Tyr Val Glu Ala Met Asp Tyr
1               5                   10

(2) INFORMATION FOR SEQ ID NO: 6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: VL chain CDR1

(xi) SEQUENCE DESCRIPTION: SEQ ID NO: 6:

Lys Ala Ser Gln Asn Val Gly Thr Asn Val Ala
1               5                   10

(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: VL chain CDR2

(xi) SEQUENCE DESCRIPTION: SEQ ID NO: 7:

Ser Ala Ser Tyr Arg Tyr Ser
1               5

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO

```
        (v) FRAGMENT TYPE: internal (vi) ORIGINAL SOURCE:
             (A) ORGANISM: VL chain CDR3

(xi) SEQUENCE DESCRIPTION: SEQ ID NO: 8:

His Gln Tyr Tyr Thr Tyr Pro Leu Phe Thr
1               5                   10

(2) INFORMATION FOR SEQ ID NO: 9:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: BGP primer (xi) SEQUENCE DESCRIPTION: SEQ ID NO: 9:

CTCAAGCTTA TGGGGCACCT C                                       21

(2) INFORMATION FOR SEQ ID NO: 10:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: BGP primer (xi) SEQUENCE DESCRIPTION: SEQ ID NO: 10:

GGTCTAGACT ATGAAGTTGG TTG                                     23

(2) INFORMATION FOR SEQ ID NO: 11:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: CEA primer (xi) SEQUENCE DESCRIPTION: SEQ ID NO: 11:

CTCAAGCTTA TGGAGTCTCC C                                       21

(2) INFORMATION FOR SEQ ID NO: 12:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: cDNA
```

(iii) HYPOTHETICAL: NO (vi) ORIGINAL SOURCE:
             (A) ORGANISM: CEA primer (xi) SEQUENCE DESCRIPTION: SEQ ID NO: 12:

GGTCTAGACT ATATCAGAGC AAC                                              23

(2) INFORMATION FOR SEQ ID NO: 13:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: Chimaera primer (xi) SEQUENCE DESCRIPTION: SEQ ID NO: 13:

GGATCGATGC AGGTCAGGTT                                                  20

(2) INFORMATION FOR SEQ ID NO: 14:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: Chimaera primer (xi) SEQUENCE DESCRIPTION: SEQ ID NO: 14:

CTCATCGATG AACCTGAGGC T                                                21

(2) INFORMATION FOR SEQ ID NO: 15:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: Chimaera primer (xi) SEQUENCE DESCRIPTION: SEQ ID NO: 15:

GGTCTAGACT ATATCAGAGC AAC                                              23

(2) INFORMATION FOR SEQ ID NO: 16:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: cDNA

```
        (iii) HYPOTHETICAL: NO (vi) ORIGINAL SOURCE:
             (A) ORGANISM: Chimaera primer (xi) SEQUENCE DESCRIPTION: SEQ ID NO: 16:

GGTCTAGACT AAGATGCAGA GAC                                               23

(2) INFORMATION FOR SEQ ID NO: 17:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: Chimaera primer (xi) SEQUENCE DESCRIPTION: SEQ ID NO: 17:

TCTGCATCTG GACTCTCACC TGGGGCC                                           27

(2) INFORMATION FOR SEQ ID NO: 18:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: Chimaera primer (xi) SEQUENCE DESCRIPTION: SEQ ID NO: 18:

GGCCCCAGGT GAGAGTCCAG ATGCAGA                                           27

(2) INFORMATION FOR SEQ ID NO: 19:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: Chimaera primer (xi) SEQUENCE DESCRIPTION: SEQ ID NO: 19:

ACAGTCTCTG CACAAGAAAA TGGC                                              24

(2) INFORMATION FOR SEQ ID NO: 20:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA
```

```
        (iii) HYPOTHETICAL: NO (vi) ORIGINAL SOURCE:
             (A) ORGANISM: Chimaera primer (xi) SEQUENCE DESCRIPTION: SEQ ID NO: 20:

GCCATTTTCT TGTGCAGAGA CTGT                                                24

(2) INFORMATION FOR SEQ ID NO: 21:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: CEA partial sequence (xi) SEQUENCE DESCRIPTION: SEQ ID NO: 21:

ATCGCCAAAA TCACG                                                          15

(2) INFORMATION FOR SEQ ID NO: 22:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: Mutagenic primer (xi) SEQUENCE DESCRIPTION: SEQ ID NO: 22:

ATCGCCGCAA TCACG                                                          15

(2) INFORMATION FOR SEQ ID NO: 23:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (vi) ORIGINAL SOURCE:
             (A) ORGANISM: CEA partial sequence (xi) SEQUENCE DESCRIPTION: SEQ ID NO: 23:

ATAGTCAAGA GCATC                                                          15

(2) INFORMATION FOR SEQ ID NO: 24:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: cDNA
```

```
    (iii) HYPOTHETICAL: NO (vi) ORIGINAL SOURCE:
         (A) ORGANISM: Mutagenic primer (xi) SEQUENCE DESCRIPTION: SEQ ID NO: 24:

ATAGTCGCGA GCATC                                                              15

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
         (A) ORGANISM: CEA partial sequence (xi) SEQUENCE DESCRIPTION: SEQ ID NO: 25:

TCTTGGCGTA TCAAT                                                              15

(2) INFORMATION FOR SEQ ID NO: 26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
         (A) ORGANISM: Mutagenic primer (xi) SEQUENCE DESCRIPTION: SEQ ID NO: 26:

TCTTGGGCTA TCAAT                                                              15

(2) INFORMATION FOR SEQ ID NO: 27:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: N-terminal (vi) ORIGINAL SOURCE:
         (A) ORGANISM: Human RF-TS3 heavy chain (xi) SEQUENCE DESCRIPTION: SEQ ID NO: 27:

Gln Val Gln Leu Val Gln Ser Gly Ser Glu Leu Lys Lys Pro Gly Ala
1               5                  10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45
```

```
Gly Trp Ile Asn Thr Asn Thr Gly Asn Pro Thr Tyr Ala Gln Gly Phe
    50              55                  60

Thr Gly Arg Phe Val Phe Ser Leu Asp Thr Ser Val Ser Thr Ala Tyr
65              70                  75                  80

Leu Gln Ile Ser Ser Leu Lys Ala Asp Asp Thr Ala Val Tyr Tyr Cys
                85                  90                  95

Ala Arg Glu Asp Ser Asn Gly Tyr Leu Ile Phe Asp Tyr Trp Asp Gln
            100                 105                 110

Gly Thr Leu Val Ile Val Ser Ser
        115                 120
```

(2) INFORMATION FOR SEQ ID NO: 28:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Humanised heavy chain (xi) SEQUENCE DESCRIPTION: SEQ ID NO: 28:

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Val Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50              55                  60

Lys Gly Arg Phe Val Phe Ser Leu Asp Thr Ser Val Ser Thr Ala Tyr
65              70                  75                  80

Leu Gln Ile Ser Ser Leu Lys Ala Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

(2) INFORMATION FOR SEQ ID NO: 29:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Hukan REI light chain (xi) SEQUENCE DESCRIPTION: SEQ ID NO: 29:

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Ala Trp Tyr Gln Gln Thr Pro Gly Lys Ala Pro Lys Leu Leu Ile
            35                  40                  45

Tyr Glu Ala Ser Asn Leu Gln Ala Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Ile Glu Ile Thr Arg
            100                 105
```

(2) INFORMATION FOR SEQ ID NO: 30:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Humanised kappa light chain (xi) SEQUENCE DESCRIPTION: SEQ ID NO: 30:

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Tyr Tyr Thr Tyr Pro Leu
                85                  90                  95

Phe Thr Phe Gly Gln Gly Thr Lys Val Glu Ile Lys Arg
            100                 105
```

(2) INFORMATION FOR SEQ ID NO: 31:

(i) SEQUENCE CHARACTERISTICS:
        (A) LENGTH: 1473 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Human biliary glycoprotein (ix) FEATURE:
        (A) NAME/KEY: CDS (B) LOCATION: 1..1392

(xi) SEQUENCE DESCRIPTION: SEQ ID NO: 31:

```
ATG GGG CAC CTC TCA GCC CCA CTT CAC AGA GTG CGT GTA CCC TGG CAG        48
Met Gly His Leu Ser Ala Pro Leu His Arg Val Arg Val Pro Trp Gln
 1               5                  10                  15

GGG CTT CTG CTC ACA GCC TCA CTT CTA ACC TTC TGG AAC CCG CCC ACC        96
Gly Leu Leu Leu Thr Ala Ser Leu Leu Thr Phe Trp Asn Pro Pro Thr
             20                  25                  30

ACT GCC CAG CTC ACT ACT GAA TCC ATG CCA TTC AAT GTT GCA GAG GGG       144
Thr Ala Gln Leu Thr Thr Glu Ser Met Pro Phe Asn Val Ala Glu Gly
         35                  40                  45

AAG GAG GTT CTT CTC CTT GTC CAC AAT CTG CCC CAG CAA CTT TTT GGC       192
Lys Glu Val Leu Leu Leu Val His Asn Leu Pro Gln Gln Leu Phe Gly
 50                  55                  60

TAC AGC TGG TAC AAA GGG GAA AGA GTG GAT GGC AAC CGT CAA ATT GTA       240
Tyr Ser Trp Tyr Lys Gly Glu Arg Val Asp Gly Asn Arg Gln Ile Val
 65                  70                  75                  80

GGA TAT GCA ATA GGA ACT CAA CAA GCT ACC CCA GGG CCC GCA AAC AGC       288
Gly Tyr Ala Ile Gly Thr Gln Gln Ala Thr Pro Gly Pro Ala Asn Ser
                 85                  90                  95

GGT CGA GAG ACA ATA TAC CCC AAT GCA TCC CTG CTG ATC CAG AAC GTC       336
Gly Arg Glu Thr Ile Tyr Pro Asn Ala Ser Leu Leu Ile Gln Asn Val
             100                 105                 110

ACC CAG AAT GAC ACA GGA TTC TAC ACC CTA CAA GTC ATA AAG TCA GAT       384
Thr Gln Asn Asp Thr Gly Phe Tyr Thr Leu Gln Val Ile Lys Ser Asp
         115                 120                 125

CTT GTG AAT GAA GAA GCA ACT GGA CAG TTC CAT GTA TAC CCG GAG CTG       432
Leu Val Asn Glu Glu Ala Thr Gly Gln Phe His Val Tyr Pro Glu Leu
     130                 135                 140

CCC AAG CCC TCC ATC TCC AGC AAC AAC TCC AAC CCT GTG GAG GAC AAG       480
Pro Lys Pro Ser Ile Ser Ser Asn Asn Ser Asn Pro Val Glu Asp Lys
145                 150                 155                 160

GAT GCT GTG GCC TTC ACC TGT GAA CCT GAG ACT CAG GAC ACA ACC TAC       528
Asp Ala Val Ala Phe Thr Cys Glu Pro Glu Thr Gln Asp Thr Thr Tyr
                 165                 170                 175

CTG TGG TGG ATA AAC AAT CAG AGC CTC CCG GTC AGT CCC AGG CTG CAG       576
Leu Trp Trp Ile Asn Asn Gln Ser Leu Pro Val Ser Pro Arg Leu Gln
             180                 185                 190

CTG TCC AAT GGC AAC AGG ACC CTC ACT CTA CTC AGT GTC ACA AGG AAT       624
Leu Ser Asn Gly Asn Arg Thr Leu Thr Leu Leu Ser Val Thr Arg Asn
         195                 200                 205

GAC ACA GGA CCC TAT GAG TGT GAA ATA CAG AAC CCA GTG AGT GCG AAC       672
Asp Thr Gly Pro Tyr Glu Cys Glu Ile Gln Asn Pro Val Ser Ala Asn
     210                 215                 220

CGC AGT GAC CCA GTC ACC TTG AAT GTC ACC TAT GGC CCG GAC ACC CCC       720
Arg Ser Asp Pro Val Thr Leu Asn Val Thr Tyr Gly Pro Asp Thr Pro
225                 230                 235                 240

ACC ATT TCC CCT TCA GAC ACC TAT TAC CGT CCA GGG GCA AAC CTC AGC       768
Thr Ile Ser Pro Ser Asp Thr Tyr Tyr Arg Pro Gly Ala Asn Leu Ser
                 245                 250                 255

CTC TCC TGC TAT GCA GCC TCT AAC CCA CCT GCA CAG TAC TCC TGG CTT       816
Leu Ser Cys Tyr Ala Ala Ser Asn Pro Pro Ala Gln Tyr Ser Trp Leu
             260                 265                 270

ATC AAT GGA ACA TTC CAG CAA AGC ACA CAA GAG CTC TTT ATC CCT AAC       864
Ile Asn Gly Thr Phe Gln Gln Ser Thr Gln Glu Leu Phe Ile Pro Asn
         275                 280                 285

ATC ACT GTG AAT AAT AGT GGA TCC TAT ACC TGC CAC GCC AAT AAC TCA       912
Ile Thr Val Asn Asn Ser Gly Ser Tyr Thr Cys His Ala Asn Asn Ser
     290                 295                 300
```

-continued

```
GTC ACT GGC TGC AAC AGG ACC ACA GTC AAG ACG ATC ATA GTC ACT GAG      960
Val Thr Gly Cys Asn Arg Thr Thr Val Lys Thr Ile Ile Val Thr Glu
305                 310                 315                 320

CTA AGT CCA GTA GTA GCA AAG CCC CAA ATC AAA GCC AGC AAG ACC ACA     1008
Leu Ser Pro Val Val Ala Lys Pro Gln Ile Lys Ala Ser Lys Thr Thr
                325                 330                 335

GTC ACA GGA GAT AAG GAC TCT GTG AAC CTG ACC TGC TCC ACA AAT GAC     1056
Val Thr Gly Asp Lys Asp Ser Val Asn Leu Thr Cys Ser Thr Asn Asp
            340                 345                 350

ACT GGA ATC TCC ATC CGT TGG TTC TTC AAA AAC CAG AGT CTC CCG TCC     1104
Thr Gly Ile Ser Ile Arg Trp Phe Phe Lys Asn Gln Ser Leu Pro Ser
        355                 360                 365

TCG GAG AGG ATG AAG CTG TCC CAG GGC AAC ACC ACC CTC AGC ATA AAC     1152
Ser Glu Arg Met Lys Leu Ser Gln Gly Asn Thr Thr Leu Ser Ile Asn
370                 375                 380

CCT GTC AAG AGG GAG GAT GCT GGG ACG TAT TGG TGT GAG GTC TTC AAC     1200
Pro Val Lys Arg Glu Asp Ala Gly Thr Tyr Trp Cys Glu Val Phe Asn
385                 390                 395                 400

CCA ATC AGT AAG AAC CAA AGC GAC CCC ATC ATG CTG AAC GTA AAC TAT     1248
Pro Ile Ser Lys Asn Gln Ser Asp Pro Ile Met Leu Asn Val Asn Tyr
                405                 410                 415

AAT GCT CTA CCA CAA GAA AAT GGC CTC TCA CCT GGG GCC ATT GCT GGC     1296
Asn Ala Leu Pro Gln Glu Asn Gly Leu Ser Pro Gly Ala Ile Ala Gly
            420                 425                 430

ATT GTG ATT GGA GTA GTG GCC CTG GTT GCT CTG ATA GCA GTA GCC CTG     1344
Ile Val Ile Gly Val Val Ala Leu Val Ala Leu Ile Ala Val Ala Leu
        435                 440                 445

GCA TGT TTT CTG CAT TTC GGG AAG ACC GGC AGC TCA GGA CCA CTC CAA     1392
Ala Cys Phe Leu His Phe Gly Lys Thr Gly Ser Ser Gly Pro Leu Gln
450                 455                 460

TGACCCACCT AACAAGATGA ATGAAGTTAC TTATCTACCC TGAACTTTGA AGCCCAGCAA   1452

CCCACACAAC CAACTTCACT T                                              1473
```

(2) INFORMATION FOR SEQ ID NO: 32:

(i) SEQUENCE CHARACTERISTICS:
        (A) LENGTH: 464 amino acids
        (B) TYPE: amino acid
        (D) TOPOLOGY: linear (ii) MOLECULE TYPE: protein (xi) SEQUENCE DESCRIPTION: SEQ ID NO: 32:

```
Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125
```

```
Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Ser Ser Gly Pro Leu Gln
    450                 455                 460

(2) INFORMATION FOR SEQ ID NO: 33:

(i) SEQUENCE CHARACTERISTICS:
        (A) LENGTH: 1103 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Human non-specific cross reacting antigen (ix) FEATURE:
```

(A) NAME/KEY: CDS
(B) LOCATION: 1..1032

(xi) SEQUENCE DESCRIPTION: SEQ ID NO: 33:

| | | | | | | | | | | | | | | | | |
|---|---|---|---|---|---|---|---|---|---|---|---|---|---|---|---|---|
| ATG | GGA | CCC | CCC | TCA | GCC | CCT | CCC | TGC | AGA | TTG | CAT | GTC | CCC | TGG | AAG | 48 |
| Met | Gly | Pro | Pro | Ser | Ala | Pro | Pro | Cys | Arg | Leu | His | Val | Pro | Trp | Lys | |
| 1 | | | | 5 | | | | | 10 | | | | | 15 | | |
| GAG | GTC | CTG | CTC | ACA | GCC | TCA | CTT | CTA | ACC | TTC | TGG | AAC | CCA | CCC | ACC | 96 |
| Glu | Val | Leu | Leu | Thr | Ala | Ser | Leu | Leu | Thr | Phe | Trp | Asn | Pro | Pro | Thr | |
| | | | | 20 | | | | | 25 | | | | | 30 | | |
| ACT | GCC | AAG | CTC | ACT | ATT | GAA | TCC | ACG | CCA | TTC | AAT | GTC | GCA | GAG | GGG | 144 |
| Thr | Ala | Lys | Leu | Thr | Ile | Glu | Ser | Thr | Pro | Phe | Asn | Val | Ala | Glu | Gly | |
| | | 35 | | | | | 40 | | | | | 45 | | | | |
| AAG | GAG | GTT | CTT | CTA | CTC | GCC | CAC | AAC | CTG | CCC | CAG | AAT | CGT | ATT | GGT | 192 |
| Lys | Glu | Val | Leu | Leu | Leu | Ala | His | Asn | Leu | Pro | Gln | Asn | Arg | Ile | Gly | |
| | 50 | | | | | 55 | | | | | 60 | | | | | |
| TAC | AGC | TGG | TAC | AAA | GCG | GAA | AGA | GTG | GAT | GGC | AAC | AGT | CTA | ATT | GTA | 240 |
| Tyr | Ser | Trp | Tyr | Lys | Ala | Glu | Arg | Val | Asp | Gly | Asn | Ser | Leu | Ile | Val | |
| 65 | | | | | 70 | | | | | 75 | | | | | 80 | |
| GGA | TAT | GTA | ATA | GGA | ACT | CAA | CAA | GCT | ACC | CCA | GGG | CCC | GCA | TAC | AGT | 288 |
| Gly | Tyr | Val | Ile | Gly | Thr | Gln | Gln | Ala | Thr | Pro | Gly | Pro | Ala | Tyr | Ser | |
| | | | | 85 | | | | | 90 | | | | | 95 | | |
| GGT | CGA | GAG | ACA | ATA | TAC | CCC | AAT | GCA | TCC | CTG | CTG | ATC | CAG | AAC | GTC | 336 |
| Gly | Arg | Glu | Thr | Ile | Tyr | Pro | Asn | Ala | Ser | Leu | Leu | Ile | Gln | Asn | Val | |
| | | | 100 | | | | | 105 | | | | | 110 | | | |
| ACC | CAG | ATT | GAC | ACA | GGA | TTC | TAT | ACC | CTA | CAA | GTC | ATA | AAG | TCA | GAT | 384 |
| Thr | Gln | Ile | Asp | Thr | Gly | Phe | Tyr | Thr | Leu | Gln | Val | Ile | Lys | Ser | Asp | |
| | | 115 | | | | | 120 | | | | | 125 | | | | |
| CTT | GTG | AAT | GAA | GAA | GCA | ACC | GGA | CAG | TTC | CAT | GTA | TAC | CCG | GAG | CTG | 432 |
| Leu | Val | Asn | Glu | Glu | Ala | Thr | Gly | Gln | Phe | His | Val | Tyr | Pro | Glu | Leu | |
| | 130 | | | | | 135 | | | | | 140 | | | | | |
| CCC | AAG | CCC | TCC | ATC | TCC | AGC | AAC | AAC | TCC | AAC | CCC | GTG | GAG | GAC | AAG | 480 |
| Pro | Lys | Pro | Ser | Ile | Ser | Ser | Asn | Asn | Ser | Asn | Pro | Val | Glu | Asp | Lys | |
| 145 | | | | | 150 | | | | | 155 | | | | | 160 | |
| GAT | GCT | GTG | GCC | TTC | ACC | TGT | GAA | CCT | GAG | GTT | CAG | AAC | ACA | ACC | TAC | 528 |
| Asp | Ala | Val | Ala | Phe | Thr | Cys | Glu | Pro | Glu | Val | Gln | Asn | Thr | Thr | Tyr | |
| | | | | 165 | | | | | 170 | | | | | 175 | | |
| GTC | TGG | TGG | GTA | AAT | GGT | CAG | AGC | CTC | CCG | GTC | AGT | CCC | AGG | CTG | CAG | 576 |
| Val | Trp | Trp | Val | Asn | Gly | Gln | Ser | Leu | Pro | Val | Ser | Pro | Arg | Leu | Gln | |
| | | | | 180 | | | | | 185 | | | | | 190 | | |
| CTG | TCC | AAT | GGC | AAC | ATG | ACC | CTC | ACT | CTA | CTC | AGC | GTC | AAA | AGG | AAC | 624 |
| Leu | Ser | Asn | Gly | Asn | Met | Thr | Leu | Thr | Leu | Leu | Ser | Val | Lys | Arg | Asn | |
| | | 195 | | | | | 200 | | | | | 205 | | | | |
| GAT | GCA | GGA | TCC | TAT | GAA | TGT | GAA | ATA | CAG | AAC | CCA | GCG | AGT | GCC | AAC | 672 |
| Asp | Ala | Gly | Ser | Tyr | Glu | Cys | Glu | Ile | Gln | Asn | Pro | Ala | Ser | Ala | Asn | |
| | 210 | | | | | 215 | | | | | 220 | | | | | |
| CGC | AGT | GAC | CCA | GTC | ACC | CTG | AAT | GTC | CTC | TAT | GGC | CCA | GAT | GGC | CCC | 720 |
| Arg | Ser | Asp | Pro | Val | Thr | Leu | Asn | Val | Leu | Tyr | Gly | Pro | Asp | Gly | Pro | |
| 225 | | | | | 230 | | | | | 235 | | | | | 240 | |
| ACC | ATT | TCC | CCC | TCA | AAG | GCC | AAT | TAC | CGT | CCA | GGG | GAA | AAT | CTG | AAC | 768 |
| Thr | Ile | Ser | Pro | Ser | Lys | Ala | Asn | Tyr | Arg | Pro | Gly | Glu | Asn | Leu | Asn | |
| | | | | 245 | | | | | 250 | | | | | 255 | | |
| CTC | TCC | TCG | CAC | GCA | GCC | TCT | AAC | CCA | CCT | GCA | CAG | TAC | TCT | TGG | TTT | 816 |
| Leu | Ser | Ser | His | Ala | Ala | Ser | Asn | Pro | Pro | Ala | Gln | Tyr | Ser | Trp | Phe | |
| | | | 260 | | | | | 265 | | | | | 270 | | | |
| ATC | AAT | GGG | ACG | TTC | CAG | CAA | TCC | ACA | CAA | GAG | CTC | TTT | ATC | CCC | AAC | 864 |
| Ile | Asn | Gly | Thr | Phe | Gln | Gln | Ser | Thr | Gln | Glu | Leu | Phe | Ile | Pro | Asn | |
| | | 275 | | | | | 280 | | | | | 285 | | | | |
| ATC | ACT | GTG | AAT | AAT | AGC | GGA | TCC | TAT | ATG | TGC | CAA | GCC | CAT | AAC | TCA | 912 |
| Ile | Thr | Val | Asn | Asn | Ser | Gly | Ser | Tyr | Met | Cys | Gln | Ala | His | Asn | Ser | |
| | 290 | | | | | 295 | | | | | 300 | | | | | |

```
GCC ACT GGC CTC AAT AGG ACC ACA GTC ACG ATG ATC ACA GTC TCT GGA        960
Ala Thr Gly Leu Asn Arg Thr Thr Val Thr Met Ile Thr Val Ser Gly
305                 310                 315                 320

AGT GCT CCT GTC CTC TCA GCT GTG GCC ACC GTC GGC ATC ACG ATT GGA       1008
Ser Ala Pro Val Leu Ser Ala Val Ala Thr Val Gly Ile Thr Ile Gly
            325                 330                 335

GTG CTG GCC AGG GTC GCT CTG ATA TAGCAGCCCT GGTGTATTTT CGATATTTCA      1062
Val Leu Ala Arg Val Ala Leu Ile
                340

GGAAGACTGG CAGATTGGAC CAGACCCTGA ATTCTTCTAG C                         1103
```

(2) INFORMATION FOR SEQ ID NO: 34:

(i) SEQUENCE CHARACTERISTICS:
        (A) LENGTH: 344 amino acids
        (B) TYPE: amino acid
        (D) TOPOLOGY: linear (ii) MOLECULE TYPE: protein (xi) SEQUENCE DESCRIPTION: SEQ ID NO: 34:

```
Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Ala His Asn Leu Pro Gln Asn Arg Ile Gly
        50                  55                  60

Tyr Ser Trp Tyr Lys Ala Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Ile Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Val Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Ser His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285
```

```
Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
                340
```

(2) INFORMATION FOR SEQ ID NO: 35:

(i) SEQUENCE CHARACTERISTICS:
        (A) LENGTH: 2097 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Human carcinoembryonic antigen (ix) FEATURE:
        (A) NAME/KEY: CDS
        (B) LOCATION: 1..2094

(xi) SEQUENCE DESCRIPTION: SEQ ID NO: 35:

```
TCG GCC CCT CCC CAC AGA TGG TGC ATC CCC TGG CAG AGG CTC CTG CTC        48
Ser Ala Pro Pro His Arg Trp Cys Ile Pro Trp Gln Arg Leu Leu Leu
  1               5                  10                  15

ACA GCC TCA CTT CTA ACC TTC TGG AAC CCG CCC ACC ACT GCC AAG CTC        96
Thr Ala Ser Leu Leu Thr Phe Trp Asn Pro Pro Thr Thr Ala Lys Leu
                 20                  25                  30

ACT ATT GAA TCC ACG CCG TTC AAT GTC GCA GAG GGG AAG GAG GTG CTT       144
Thr Ile Glu Ser Thr Pro Phe Asn Val Ala Glu Gly Lys Glu Val Leu
             35                  40                  45

CTA CTT GTC CAC AAT CTG CCC CAG CAT CTT TTT GGC TAC AGC TGG TAC       192
Leu Leu Val His Asn Leu Pro Gln His Leu Phe Gly Tyr Ser Trp Tyr
         50                  55                  60

AAA GGT GAA AGA GTG GAT GGC AAC CGT CAA ATT ATA GGA TAT GTA ATA       240
Lys Gly Glu Arg Val Asp Gly Asn Arg Gln Ile Ile Gly Tyr Val Ile
 65                  70                  75                  80

GGA ACT CAA CAA GCT ACC CCA GGG CCC GCA TAC AGT GGT CGA GAG ATA       288
Gly Thr Gln Gln Ala Thr Pro Gly Pro Ala Tyr Ser Gly Arg Glu Ile
                 85                  90                  95

ATA TAC CCC AAT GCA TCC CTG CTG ATC CAG AAC ATC ATC CAG AAT GAC       336
Ile Tyr Pro Asn Ala Ser Leu Leu Ile Gln Asn Ile Ile Gln Asn Asp
            100                 105                 110

ACA GGA TTC TAC ACC CTA CAC GTC ATA AAG TCA GAT CTT GTG AAT GAA       384
Thr Gly Phe Tyr Thr Leu His Val Ile Lys Ser Asp Leu Val Asn Glu
        115                 120                 125

GAA GCA ACT GGC CAG TTC CGG GTA TAC CCG GAG CTG CCC AAG CCC TCC       432
Glu Ala Thr Gly Gln Phe Arg Val Tyr Pro Glu Leu Pro Lys Pro Ser
    130                 135                 140

ATC TCC AGC AAC AAC TCC AAA CCC GTG GAG GAC AAG GAT GCT GTG GCC       480
Ile Ser Ser Asn Asn Ser Lys Pro Val Glu Asp Lys Asp Ala Val Ala
145                 150                 155                 160

TTC ACC TGT GAA CCT GAG ACT CAG GAC GCA ACC TAC CTG TGG TGG GTA       528
Phe Thr Cys Glu Pro Glu Thr Gln Asp Ala Thr Tyr Leu Trp Trp Val
                165                 170                 175

AAC AAT CAG AGC CTC CCG GTC AGT CCC AGG CTG CAG CTG TCC AAT GGC       576
```

```
          Asn Asn Gln Ser Leu Pro Val Ser Pro Arg Leu Gln Leu Ser Asn Gly
                          180                 185                 190

AAC AGG ACC CTC ACT CTA TTC AAT GTC ACA AGA AAT GAC ACA GCA AGC             624
Asn Arg Thr Leu Thr Leu Phe Asn Val Thr Arg Asn Asp Thr Ala Ser
            195                 200                 205

TAC AAA TGT GAA ACC CAG AAC CCA GTG AGT GCC AGG CGC AGT GAT TCA             672
Tyr Lys Cys Glu Thr Gln Asn Pro Val Ser Ala Arg Arg Ser Asp Ser
210                 215                 220

GTC ATC CTG AAT GTC CTC TAT GGC CCG GAT GCC CCC ACC ATT TCC CCT             720
Val Ile Leu Asn Val Leu Tyr Gly Pro Asp Ala Pro Thr Ile Ser Pro
225                 230                 235                 240

CTA AAC ACA TCT TAC AGA TCA GGG GAA AAT CTG AAC CTC TCC TGC CAC             768
Leu Asn Thr Ser Tyr Arg Ser Gly Glu Asn Leu Asn Leu Ser Cys His
                245                 250                 255

GCA GCC TCT AAC CCA CCT GCA CAG TAC TCT TGG TTT GTC AAT GGG ACT             816
Ala Ala Ser Asn Pro Pro Ala Gln Tyr Ser Trp Phe Val Asn Gly Thr
                260                 265                 270

TTC CAG CAA TCC ACC CAA GAG CTC TTT ATC CCC AAC ATC ACT GTG AAT             864
Phe Gln Gln Ser Thr Gln Glu Leu Phe Ile Pro Asn Ile Thr Val Asn
            275                 280                 285

AAT AGT GGA TCC TAT ACG TGC CAA GCC CAT AAC TCA GAC ACT GGC CTC             912
Asn Ser Gly Ser Tyr Thr Cys Gln Ala His Asn Ser Asp Thr Gly Leu
            290                 295                 300

AAT AGG ACC ACA GTC ACG ACG ATC ACA GTC TAT GCA GAG CCA CCC AAA             960
Asn Arg Thr Thr Val Thr Thr Ile Thr Val Tyr Ala Glu Pro Pro Lys
305                 310                 315                 320

CCC TTC ATC ACC AGC AAC AAC TCC AAC CCC GTG GAG GAT GAG GAT GCT            1008
Pro Phe Ile Thr Ser Asn Asn Ser Asn Pro Val Glu Asp Glu Asp Ala
                325                 330                 335

GTA GCC TTA ACC TGT GAA CCT GAG ATT CAG AAC ACA ACC TAC CTG TGG            1056
Val Ala Leu Thr Cys Glu Pro Glu Ile Gln Asn Thr Thr Tyr Leu Trp
                340                 345                 350

TGG GTA AAT AAT CAG AGC CTC CCG GTC AGT CCC AGG CTG CAG CTG TCC            1104
Trp Val Asn Asn Gln Ser Leu Pro Val Ser Pro Arg Leu Gln Leu Ser
            355                 360                 365

AAT GAC AAC AGG ACC CTC ACT CTA CTC AGT GTC ACA AGG AAT GAT GTA            1152
Asn Asp Asn Arg Thr Leu Thr Leu Leu Ser Val Thr Arg Asn Asp Val
370                 375                 380

GGA CCC TAT GAG TGT GGA ATC CAG AAC GAA TTA AGT GTT GAC CAC AGC            1200
Gly Pro Tyr Glu Cys Gly Ile Gln Asn Glu Leu Ser Val Asp His Ser
385                 390                 395                 400

GAC CCA GTC ATC CTG AAT GTC CTC TAT GGC CCA GAC GAC CCC ACC ATT            1248
Asp Pro Val Ile Leu Asn Val Leu Tyr Gly Pro Asp Asp Pro Thr Ile
                405                 410                 415

TCC CCC TCA TAC ACC TAT TAC CGT CCA GGG GTG AAC CTC AGC CTC TCC            1296
Ser Pro Ser Tyr Thr Tyr Tyr Arg Pro Gly Val Asn Leu Ser Leu Ser
                420                 425                 430

TGC CAT GCA GCC TCT AAC CCA CCT GCA CAG TAT TCT TGG CTG ATT GAT            1344
Cys His Ala Ala Ser Asn Pro Pro Ala Gln Tyr Ser Trp Leu Ile Asp
            435                 440                 445

GGG AAC ATC CAG CAA CAC ACA CAA GAG CTC TTT ATC TCC AAC ATC ACT            1392
Gly Asn Ile Gln Gln His Thr Gln Glu Leu Phe Ile Ser Asn Ile Thr
            450                 455                 460

GAG AAG AAC AGC GGA CTC TAT ACC TGC CAG GCC AAT AAC TCA GCC AGT            1440
Glu Lys Asn Ser Gly Leu Tyr Thr Cys Gln Ala Asn Asn Ser Ala Ser
465                 470                 475                 480

GGC CAC AGC AGG ACT ACA GTC AAG ACA ATC ACA GTC TCT GCG GAG CTG            1488
Gly His Ser Arg Thr Thr Val Lys Thr Ile Thr Val Ser Ala Glu Leu
                485                 490                 495

CCC AAG CCC TCC ATC TCC AGC AAC AAC TCC AAA CCC GTG GAG GAC AAG            1536
```

```
Pro Lys Pro Ser Ile Ser Ser Asn Asn Ser Lys Pro Val Glu Asp Lys
            500                 505                 510

GAT GCT GTG GCC TTC ACC TGT GAA CCT GAG GCT CAG AAC ACA ACC TAC       1584
Asp Ala Val Ala Phe Thr Cys Glu Pro Glu Ala Gln Asn Thr Thr Tyr
            515                 520                 525

CTG TGG TGG GTA AAT GGT CAG AGC CTC CCA GTC AGT CCC AGG CTG CAG       1632
Leu Trp Trp Val Asn Gly Gln Ser Leu Pro Val Ser Pro Arg Leu Gln
            530                 535                 540

CTG TCC AAT GGC AAC AGG ACC CTC ACT CTA TTC AAT GTC ACA AGA AAT       1680
Leu Ser Asn Gly Asn Arg Thr Leu Thr Leu Phe Asn Val Thr Arg Asn
545                 550                 555                 560

GAC GCA AGA GCC TAT GTA TGT GGA ATC CAG AAC TCA GTG AGT GCA AAC       1728
Asp Ala Arg Ala Tyr Val Cys Gly Ile Gln Asn Ser Val Ser Ala Asn
            565                 570                 575

CGC AGT GAC CCA GTC ACC CTG GAT GTC CTC TAT GGG CCG GAC ACC CCC       1776
Arg Ser Asp Pro Val Thr Leu Asp Val Leu Tyr Gly Pro Asp Thr Pro
            580                 585                 590

ATC ATT TCC CCC CCA GAC TCG TCT TAC CTT TCG GGA GCG AAC CTC AAC       1824
Ile Ile Ser Pro Pro Asp Ser Ser Tyr Leu Ser Gly Ala Asn Leu Asn
            595                 600                 605

CTC TCC TGC CAC TCG GCC TCT AAC CCA TCC CCG CAG TAT TCT TGG CGT       1872
Leu Ser Cys His Ser Ala Ser Asn Pro Ser Pro Gln Tyr Ser Trp Arg
            610                 615                 620

ATC AAT GGG ATA CCG CAG CAA CAC ACA CAA GTT CTC TTT ATC GCC AAA       1920
Ile Asn Gly Ile Pro Gln Gln His Thr Gln Val Leu Phe Ile Ala Lys
625                 630                 635                 640

ATC ACG CCA AAT AAT AAC GGG ACC TAT GCC TGT TTT GTC TCT AAC TTG       1968
Ile Thr Pro Asn Asn Asn Gly Thr Tyr Ala Cys Phe Val Ser Asn Leu
            645                 650                 655

GCT ACT GGC CGC AAT AAT TCC ATA GTC AAG AGC ATC ACA GTC TCT GCA       2016
Ala Thr Gly Arg Asn Asn Ser Ile Val Lys Ser Ile Thr Val Ser Ala
            660                 665                 670

TCT GGA ACT TCT CCT GGT CTC TCA GCT GGG GCC ACT GTC GGC ATC ATG       2064
Ser Gly Thr Ser Pro Gly Leu Ser Ala Gly Ala Thr Val Gly Ile Met
            675                 680                 685

ATT GGA GTG CTG GTT GGG GTT GCT CTG ATA TAG                           2097
Ile Gly Val Leu Val Gly Val Ala Leu Ile
            690                 695
```

(2) INFORMATION FOR SEQ ID NO: 36:

(i) SEQUENCE CHARACTERISTICS:
        (A) LENGTH: 698 amino acids
        (B) TYPE: amino acid
        (D) TOPOLOGY: linear (ii) MOLECULE TYPE: protein (xi) SEQUENCE DESCRIPTION: SEQ ID NO: 36:

```
Ser Ala Pro Pro His Arg Trp Cys Ile Pro Trp Gln Arg Leu Leu Leu
1               5                   10                  15

Thr Ala Ser Leu Leu Thr Phe Trp Asn Pro Thr Thr Ala Lys Leu
            20                  25                  30

Thr Ile Glu Ser Thr Pro Phe Asn Val Ala Glu Gly Lys Glu Val Leu
            35                  40                  45

Leu Leu Val His Asn Leu Pro Gln His Leu Phe Gly Tyr Ser Trp Tyr
        50                  55                  60

Lys Gly Glu Arg Val Asp Gly Asn Arg Gln Ile Ile Gly Tyr Val Ile
65                  70                  75                  80

Gly Thr Gln Gln Ala Thr Pro Gly Pro Ala Tyr Ser Gly Arg Glu Ile
            85                  90                  95
```

-continued

```
Ile Tyr Pro Asn Ala Ser Leu Leu Ile Gln Asn Ile Ile Gln Asn Asp
            100                 105                 110

Thr Gly Phe Tyr Thr Leu His Val Ile Lys Ser Asp Leu Val Asn Glu
        115                 120                 125

Glu Ala Thr Gly Gln Phe Arg Val Tyr Pro Glu Leu Pro Lys Pro Ser
130                 135                 140

Ile Ser Ser Asn Asn Ser Lys Pro Val Glu Asp Lys Asp Ala Val Ala
145                 150                 155                 160

Phe Thr Cys Glu Pro Glu Thr Gln Asp Ala Thr Tyr Leu Trp Trp Val
                165                 170                 175

Asn Asn Gln Ser Leu Pro Val Ser Pro Arg Leu Gln Leu Ser Asn Gly
            180                 185                 190

Asn Arg Thr Leu Thr Leu Phe Asn Val Thr Arg Asn Asp Thr Ala Ser
        195                 200                 205

Tyr Lys Cys Glu Thr Gln Asn Pro Val Ser Ala Arg Arg Ser Asp Ser
210                 215                 220

Val Ile Leu Asn Val Leu Tyr Gly Pro Asp Ala Pro Thr Ile Ser Pro
225                 230                 235                 240

Leu Asn Thr Ser Tyr Arg Ser Gly Glu Asn Leu Asn Leu Ser Cys His
                245                 250                 255

Ala Ala Ser Asn Pro Pro Ala Gln Tyr Ser Trp Phe Val Asn Gly Thr
            260                 265                 270

Phe Gln Gln Ser Thr Gln Glu Leu Phe Ile Pro Asn Ile Thr Val Asn
        275                 280                 285

Asn Ser Gly Ser Tyr Thr Cys Gln Ala His Asn Ser Asp Thr Gly Leu
290                 295                 300

Asn Arg Thr Thr Val Thr Thr Ile Thr Val Tyr Ala Glu Pro Pro Lys
305                 310                 315                 320

Pro Phe Ile Thr Ser Asn Asn Ser Asn Pro Val Glu Asp Glu Asp Ala
                325                 330                 335

Val Ala Leu Thr Cys Glu Pro Glu Ile Gln Asn Thr Thr Tyr Leu Trp
            340                 345                 350

Trp Val Asn Asn Gln Ser Leu Pro Val Ser Pro Arg Leu Gln Leu Ser
        355                 360                 365

Asn Asp Asn Arg Thr Leu Thr Leu Leu Ser Val Thr Arg Asn Asp Val
370                 375                 380

Gly Pro Tyr Glu Cys Gly Ile Gln Asn Glu Leu Ser Val Asp His Ser
385                 390                 395                 400

Asp Pro Val Ile Leu Asn Val Leu Tyr Gly Pro Asp Asp Pro Thr Ile
                405                 410                 415

Ser Pro Ser Tyr Thr Tyr Tyr Arg Pro Gly Val Asn Leu Ser Leu Ser
            420                 425                 430

Cys His Ala Ala Ser Asn Pro Pro Ala Gln Tyr Ser Trp Leu Ile Asp
        435                 440                 445

Gly Asn Ile Gln Gln His Thr Gln Glu Leu Phe Ile Ser Asn Ile Thr
450                 455                 460

Glu Lys Asn Ser Gly Leu Tyr Thr Cys Gln Ala Asn Asn Ser Ala Ser
465                 470                 475                 480

Gly His Ser Arg Thr Thr Val Lys Thr Ile Thr Val Ser Ala Glu Leu
                485                 490                 495

Pro Lys Pro Ser Ile Ser Ser Asn Asn Ser Lys Pro Val Glu Asp Lys
            500                 505                 510

Asp Ala Val Ala Phe Thr Cys Glu Pro Glu Ala Gln Asn Thr Thr Tyr
```

```
                515                 520                 525
Leu Trp Trp Val Asn Gly Gln Ser Leu Pro Val Ser Pro Arg Leu Gln
    530                 535                 540

Leu Ser Asn Gly Asn Arg Thr Leu Thr Leu Phe Asn Val Thr Arg Asn
545                 550                 555                 560

Asp Ala Arg Ala Tyr Val Cys Gly Ile Gln Asn Ser Val Ser Ala Asn
                565                 570                 575

Arg Ser Asp Pro Val Thr Leu Asp Val Leu Tyr Gly Pro Asp Thr Pro
                580                 585                 590

Ile Ile Ser Pro Pro Asp Ser Ser Tyr Leu Ser Gly Ala Asn Leu Asn
                595                 600                 605

Leu Ser Cys His Ser Ala Ser Asn Pro Ser Pro Gln Tyr Ser Trp Arg
    610                 615                 620

Ile Asn Gly Ile Pro Gln Gln His Thr Gln Val Leu Phe Ile Ala Lys
625                 630                 635                 640

Ile Thr Pro Asn Asn Asn Gly Thr Tyr Ala Cys Phe Val Ser Asn Leu
                645                 650                 655

Ala Thr Gly Arg Asn Asn Ser Ile Val Lys Ser Ile Thr Val Ser Ala
                660                 665                 670

Ser Gly Thr Ser Pro Gly Leu Ser Ala Gly Ala Thr Val Gly Ile Met
    675                 680                 685

Ile Gly Val Leu Val Gly Val Ala Leu Ile
690                 695

(2) INFORMATION FOR SEQ ID NO: 37:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Mouse PR1A3 kappa light chain (ix) FEATURE:
        (A) NAME/KEY: CDS
        (B) LOCATION: 1..396

(xi) SEQUENCE DESCRIPTION: SEQ ID NO: 37:

ATG GGC ATC AAG ATG GAG TCA CAT TCC CTG GTC TTT GTA TAC ATG TTG        48
Met Gly Ile Lys Met Glu Ser His Ser Leu Val Phe Val Tyr Met Leu
  1               5                  10                  15

CTG TGG TTG TCT GGT GTT GAT GGA GAC ATT GTG ATG ACC CAG TCT CAA        96
Leu Trp Leu Ser Gly Val Asp Gly Asp Ile Val Met Thr Gln Ser Gln
             20                  25                  30

AGA TTC ATG TCC ACA TCA GTA GGA GAC AGG GTC AGC GTC ACC TGC AAG       144
Arg Phe Met Ser Thr Ser Val Gly Asp Arg Val Ser Val Thr Cys Lys
         35                  40                  45

GCC AGT CAG AAT GTG GGT ACT AAT GTT GCC TGG TAT CAA CAG AAA CCA       192
Ala Ser Gln Asn Val Gly Thr Asn Val Ala Trp Tyr Gln Gln Lys Pro
     50                  55                  60

GGA CAA TCC CCT AAA GCA CTG ATT TAC TCG GCA TCC TAC CGG TAC AGT       240
Gly Gln Ser Pro Lys Ala Leu Ile Tyr Ser Ala Ser Tyr Arg Tyr Ser
 65                  70                  75                  80

GGA GTC CCT GAT CGC TTC ACA GGC AGT GGA TCT GGG ACA GAT TTC ACT       288
Gly Val Pro Asp Arg Phe Thr Gly Ser Gly Ser Gly Thr Asp Phe Thr
                 85                  90                  95
```

```
CTC ACC ATC AGC AAT GTA CAG TCT GAA GAC TTG GCG GAG TAT TTC TGT     336
Leu Thr Ile Ser Asn Val Gln Ser Glu Asp Leu Ala Glu Tyr Phe Cys
        100                 105                 110

CAC CAA TAT TAC ACC TAT CCT CTA TTC ACG TTC GGC TCG GGG ACA AAG     384
His Gln Tyr Tyr Thr Tyr Pro Leu Phe Thr Phe Gly Ser Gly Thr Lys
        115                 120                 125

TTG GAA ATG AAA                                                     396
Leu Glu Met Lys
    130
```

(2) INFORMATION FOR SEQ ID NO: 38:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO: 38:

```
Met Gly Ile Lys Met Glu Ser His Ser Leu Val Phe Val Tyr Met Leu
 1               5                  10                  15

Leu Trp Leu Ser Gly Val Asp Gly Asp Ile Val Met Thr Gln Ser Gln
            20                  25                  30

Arg Phe Met Ser Thr Ser Val Gly Asp Arg Val Ser Val Thr Cys Lys
        35                  40                  45

Ala Ser Gln Asn Val Gly Thr Asn Val Ala Trp Tyr Gln Gln Lys Pro
    50                  55                  60

Gly Gln Ser Pro Lys Ala Leu Ile Tyr Ser Ala Ser Tyr Arg Tyr Ser
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Glu Tyr Phe Cys
        100                 105                 110

His Gln Tyr Tyr Thr Tyr Pro Leu Phe Thr Phe Gly Ser Gly Thr Lys
        115                 120                 125

Leu Glu Met Lys
    130
```

(2) INFORMATION FOR SEQ ID NO: 39:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Mouse PR1A3 heavy chain (ix) FEATURE:
        (A) NAME/KEY: CDS
        (B) LOCATION: 1..417

(xi) SEQUENCE DESCRIPTION: SEQ ID NO: 39:

```
ATG GGA TGG AGC TGT ATC ATG CTC TTC TTG GCA GCA ACA GCT ACA GGT     48
Met Gly Trp Ser Cys Ile Met Leu Phe Leu Ala Ala Thr Ala Thr Gly
 1               5                  10                  15

GTC CAC TCC CAG GTG AAG CTG CAG CAG TCA GGA CCT GAG TTG AAG AAG     96
Val His Ser Gln Val Lys Leu Gln Gln Ser Gly Pro Glu Leu Lys Lys
```

```
                   20                      25                      30
CCT GGA GAG ACA GTC AAG ATC TCC TGC AAG GCT TCT GGA TAT ACC TTC         144
Pro Gly Glu Thr Val Lys Ile Ser Cys Lys Ala Ser Gly Tyr Thr Phe
            35                      40                      45

ACA GTG TTT GGA ATG AAC TGG GTG AAG CAG GCT CCT GGA AAG GGT TTA         192
Thr Val Phe Gly Met Asn Trp Val Lys Gln Ala Pro Gly Lys Gly Leu
        50                      55                      60

AAG TGG ATG GGC TGG ATA AAC ACC AAA ACT GGA GAG GCA ACA TAT GTT         240
Lys Trp Met Gly Trp Ile Asn Thr Lys Thr Gly Glu Ala Thr Tyr Val
 65                      70                      75                  80

GAA GAG TTT AAG GGA CGG TTT GCC TTC TCT TTG GAG ACC TCT GCC ACC         288
Glu Glu Phe Lys Gly Arg Phe Ala Phe Ser Leu Glu Thr Ser Ala Thr
                85                      90                      95

ACT GCC TAT TTG CAG ATC AAC AAC CTC AAA AAT GAG GAC ACG GCT AAA         336
Thr Ala Tyr Leu Gln Ile Asn Asn Leu Lys Asn Glu Asp Thr Ala Lys
            100                     105                     110

TAT TTC TGT GCA AGA TGG GAC TTC TAT GAT TAC GTG GAG GCT ATG GAC         384
Tyr Phe Cys Ala Arg Trp Asp Phe Tyr Asp Tyr Val Glu Ala Met Asp
        115                     120                     125

TAC TGG GGC CAA GGG ACC ACG GTC ACC GTC TCC                             417
Tyr Trp Gly Gln Gly Thr Thr Val Thr Val Ser
130                     135
```

(2) INFORMATION FOR SEQ ID NO: 40:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO: 40:

```
Met Gly Trp Ser Cys Ile Met Leu Phe Leu Ala Ala Thr Ala Thr Gly
 1               5                      10                      15

Val His Ser Gln Val Lys Leu Gln Gln Ser Gly Pro Glu Leu Lys Lys
                20                      25                      30

Pro Gly Glu Thr Val Lys Ile Ser Cys Lys Ala Ser Gly Tyr Thr Phe
            35                      40                      45

Thr Val Phe Gly Met Asn Trp Val Lys Gln Ala Pro Gly Lys Gly Leu
        50                      55                      60

Lys Trp Met Gly Trp Ile Asn Thr Lys Thr Gly Glu Ala Thr Tyr Val
 65                      70                      75                  80

Glu Glu Phe Lys Gly Arg Phe Ala Phe Ser Leu Glu Thr Ser Ala Thr
                85                      90                      95

Thr Ala Tyr Leu Gln Ile Asn Asn Leu Lys Asn Glu Asp Thr Ala Lys
            100                     105                     110

Tyr Phe Cys Ala Arg Trp Asp Phe Tyr Asp Tyr Val Glu Ala Met Asp
        115                     120                     125

Tyr Trp Gly Gln Gly Thr Thr Val Thr Val Ser
130                     135
```